United States Patent [19]
Kato et al.

[11] Patent Number: 6,093,294
[45] Date of Patent: Jul. 25, 2000

[54] GAS SENSOR AND GAS CONCENTRATION CONTROLLER

[75] Inventors: Nobuhide Kato, Ama-Gun; Noriyuki Ina, Okazaki, both of Japan

[73] Assignee: NGK Insulators, Ltd., Japan

[21] Appl. No.: 08/882,071

[22] Filed: Jun. 25, 1997

[30] Foreign Application Priority Data

Jun. 28, 1996 [JP] Japan .................................. 8-170246

[51] Int. Cl.⁷ ................................................ G01N 27/407
[52] U.S. Cl. ..................... 204/425; 204/426; 205/781; 205/784.5; 205/786.5; 205/788
[58] Field of Search ........................... 204/412, 421–429; 205/780.5, 781, 783.5, 784, 784.5, 785, 788, 786.5

[56] References Cited

U.S. PATENT DOCUMENTS

| | | |
|---|---|---|
| 4,824,549 | 4/1989 | Hamada et al. . |
| 4,927,517 | 5/1990 | Mizutani et al. ........................ 204/412 |
| 4,990,235 | 2/1991 | Chujo ...................................... 204/424 |
| 5,034,112 | 7/1991 | Murase et al. . |
| 5,558,752 | 9/1996 | Wang et al. ............................. 204/401 |
| 5,672,811 | 9/1997 | Kato et al. .............................. 204/426 |

FOREIGN PATENT DOCUMENTS

| | | |
|---|---|---|
| 0444674 | 9/1991 | European Pat. Off. . |
| 0678740 | 10/1995 | European Pat. Off. . |
| 079693 | 4/1997 | European Pat. Off. . |
| 2194846 | 3/1988 | United Kingdom . |
| 2288873 | 11/1995 | United Kingdom . |

*Primary Examiner*—T. Tung
*Attorney, Agent, or Firm*—Parkhurst & Wendel, L.L.

[57] ABSTRACT

Disclosed are a gas sensor and a gas concentration controller each comprising a comparative amplifier for comparing a reference voltage with a terminal voltage between a reference electrode and an inner pumping electrode to obtain a difference therebetween, and amplifying the difference with a predetermined gain to make an output. Wiring connection is arranged so that the output voltage from the comparative amplifier is applied, as a pumping voltage to an oxygen pump, between the electrode and an outer pumping electrode. A resistor for detecting a pumping current is inserted and connected between an output terminal of the comparative amplifier and the electrode of the oxygen pump. A short circuit is formed between both ends of the resistor by using a capacitor. One electrode of the capacitor is connected to a non-inverting terminal of a differential amplifier, and the other electrode is connected to an inverting terminal of the differential amplifier. Accordingly, it is possible to effectively avoid the oscillation phenomenon of the feedback control system for the oxygen pump, and absorb the error in the amount corresponding to voltage drop resulting from the impedance of the oxygen pump.

15 Claims, 22 Drawing Sheets

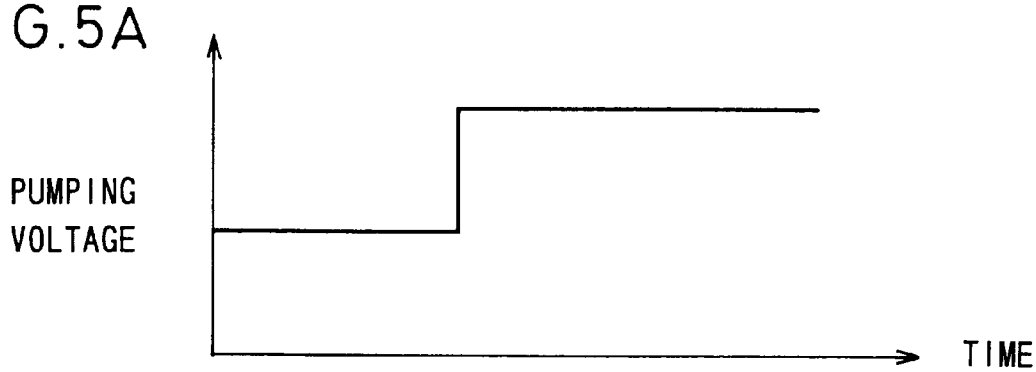
FIG.5A PUMPING VOLTAGE
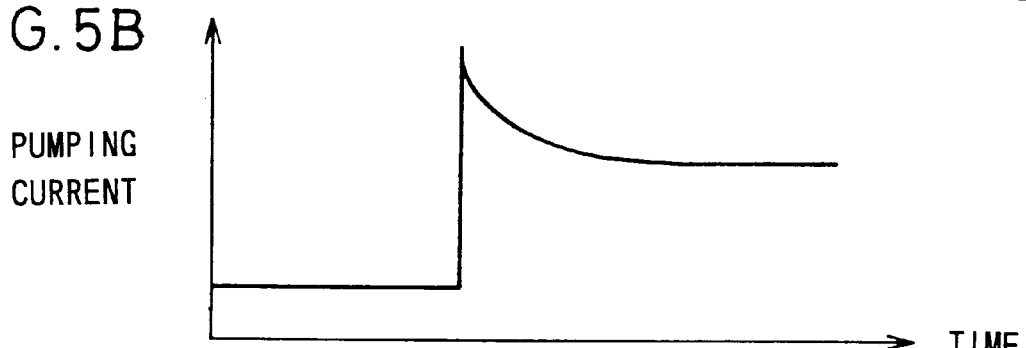
FIG.5B PUMPING CURRENT
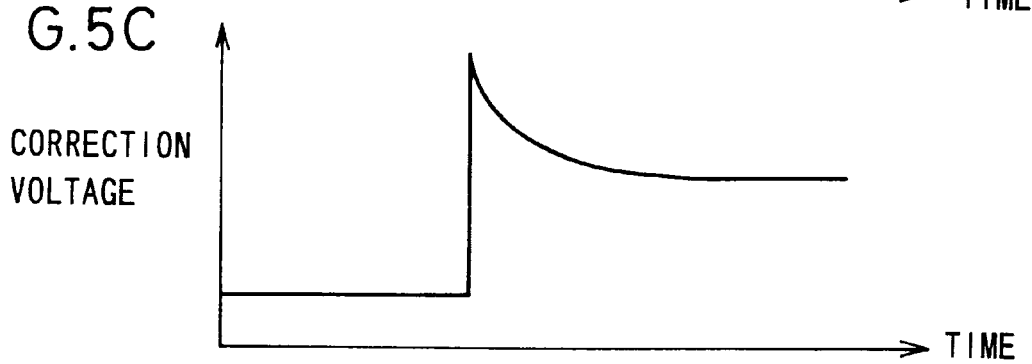
FIG.5C CORRECTION VOLTAGE

1

GAS SENSOR AND GAS CONCENTRATION CONTROLLER

BACKGROUND OF THE INVENTION

1. Field of the Invention

The present invention relates to a gas sensor and a gas concentration controller used to measure oxides such as NO, $NO_2$, $SO_2$, $CO_2$, and $H_2O$ contained in, for example, atmospheric air and exhaust gas discharged from vehicles or automobiles, and inflammable gases such as CO and CnHm.

2. Description of the Related Art

In recent years, exhaust gas, which is discharged from vehicles or automobiles such as gasoline-fueled automobiles and diesel powered automobiles, contains nitrogen oxides (NOx) such as nitrogen monoxide (NO) and nitrogen dioxide ($NO_2$), as well as carbon monoxide (CO), carbon dioxide ($CO_2$), water ($H_2O$), hydrocarbon (HC), hydrogen ($H_2$), oxygen ($O_2$) and so on. In such exhaust gas, about 80% of the entire NOx is occupied by NO, and about 95% of the entire NOx is occupied by NO and $NO_2$.

The three way catalyst, which is used to clean HC, CO, and NOx contained in the exhaust gas, exhibits its maximum cleaning efficiency in the vicinity of the theoretical air fuel ratio (A/F=14.6). If A/F is controlled to be not less than 16, the amount of produced NOx is decreased. However, the cleaning efficiency of the catalyst is lowered, and consequently the amount of discharged NOx is apt to increase.

Recently, in order to effectively utilize fossil fuel and avoid global warming, the market demand increases, for example, in that the discharge amount of $CO_2$ should be suppressed. In order to respond to such a demand, it becomes more necessary to improve the fuel efficiency. In response to such a demand, for example, the lean burn engine and the catalyst for cleaning NOx are being researched. Especially, the need for a NOx sensor increases.

A conventional NOx analyzer has been hitherto known as an instrument for detecting NOx. The conventional NOx analyzer is operated to measure a characteristic inherent in NOx, based on the use of chemical luminous analysis. However, the conventional NOx analyzer is inconvenient in that the instrument itself is extremely large and expensive.

The conventional NOx analyzer requires frequent maintenance because optical parts are used to detect NOx. Further, when the conventional NOx analyzer is used, any sampling operation should be performed for measurement of NOx, wherein it is impossible to directly insert a detecting element itself into a fluid. Therefore, the conventional NOx analyzer is not suitable for analyzing transient phenomena such as those occur in the exhaust gas discharged from an automobile, in which the condition frequently varies.

In order to dissolve the inconveniences as described above, there has been suggested a sensor for measuring a desired gas component in exhaust gas by using a substrate composed of an oxygen ion-conductive solid electrolyte.

The suggested conventional gas sensor is exemplified by a limiting current type oxygen sensor based on the use of an oxygen pump as shown in FIG. 17. The oxygen sensor comprises three stacked solid electrolyte layers 100a to 100c. The second solid electrolyte layer 100b is used as a spacer layer to possess a reference gas-introducing space 102 formed by side surfaces of the spacer layer 100b, an upper surface of the lowermost solid electrolyte layer 100a, and a lower surface of the uppermost solid electrolyte layer 100c. For example, the atmospheric air is introduced into the reference gas-introducing space 102 which is provided with an inner pumping electrode 104a formed on its inner wall surface. An outer pumping electrode 104b is formed on an upper surface of the uppermost solid electrolyte layer 100c. A diffusion rate-determining layer 106 is formed so that the electrode 104b is covered therewith. An oxygen pump 108 is constructed by the outer pumping electrode 104, the inner pumping electrode 104a, and the solid electrolyte layer 100c intervening therebetween.

Upon the operation of the oxygen sensor, a constant pumping voltage Vp is applied between the inner pumping electrode 104a and the outer pumping electrode 104b. A current flowing between the both electrodes 104a, 104b is measured by using an ammeter 110. Thus the oxygen concentration in exhaust gas is measured.

Upon the operation of the sensor described above, the constant pumping voltage Vp is applied. Therefore, for example, as shown in FIG. 18, when the oxygen concentration is increased, the amount corresponding to electromotive force is decreased by the amount corresponding to impedance of the oxygen pump 108. As a result, an oxygen concentration to be substantially controlled is increased. In such a situation, it is impossible to accurately measure the oxygen concentration (the oxygen concentration is higher at Point B than at Point A in FIG. 18).

On the other hand, Japanese Utility Model Publication No. 7-45004 discloses a system in which a voltage corresponding to a pumping current is generated by using an operational amplifier. The voltage is returned to the operational amplifier via a feedback resistor, and it is supplied to a resistor which is connected to a power source in series. When the pumping current is increased, the voltage generated by the resistor is superimposed and applied to the pump.

This system comprises a circuit as shown in FIG. 19. The output of the operational amplifier OP is returned to an input terminal on a side of an air electrode (inner pumping electrode 104a) via the feedback resistor R1 so that the voltage corresponding to the pumping current is generated at an output point A. On the other hand, the output is returned to an input terminal on a side of an outer pumping electrode 104b via the resistor R2, and the current is allowed to flow via the resistor r so that an amount of voltage generated in the resistor r is superimposed on a power source voltage $V_E$.

When the resistor connected to the power source in series is appropriately designed, a voltage corresponding (actual pump impedance×pumping current) is superimposed on the pumping voltage Vp so that the operation point is set at any of certain flat portions on limiting current characteristic curves as shown in FIG. 20. Thus the oxygen concentration is measured with a high degree of accuracy.

However, in the case of the conventional gas sensor, when the oxygen concentration in a measurement gas is increased, the amount corresponding to voltage drop is increased, and it becomes far larger than the amount corresponding to electromotive force. Therefore, it is difficult to operate the gas sensor at an operation point which accurately corresponds to a certain electromotive force.

When the temperature of exhaust gas greatly changes as in the automobile, the gas sensor is provided with a heater, for which a mechanism for controlling the electric power to be supplied to the heater is provided, in some cases. Even when such a system is adopted, the impedance of the oxygen pump 108 is slightly changed. When the pumping current is increased, a large error occurs in correction for the amount corresponding to voltage drop. As a result, it is difficult to correctly measure the high oxygen concentration.

This problem is most serious especially when the oxygen pump 108 is used as an oxygen concentration controller.

When the oxygen pump 108 is used as an oxygen pump, even if the oxygen concentration in the measurement gas is increased, the pumping current is increased, and the oxygen concentration in the measurement space is increased from $10^{-10}$ atm to $10^{-3}$ atm, then the change in current based on the change in oxygen concentration is about several % at most, as compared with the increased pumping current. However, when the oxygen pump 108 is used as an oxygen concentration controller, the change in oxygen concentration is exactly the large change from $10^{-10}$ atm to $10^{-3}$ atm as it is.

Practically, a problem arises in that it is impossible to superimpose the voltage corresponding to (pump impedance×pumping current) on the pumping voltage, and hence the accuracy is further decreased. FIG. 21 shows such a situation as analyzed in a comparative test. In this comparative test, the temperature of the gas sensor is adjusted so that the impedance of the oxygen pump 108 is 100Ω in any case.

In the conventional method (Japanese Utility Model Publication No. 7-45004), the correction voltage is ideally (100Ω×pumping current) because the impedance of the oxygen pump 108 is 100Ω. However, in fact, correction is successful for only (50Ω×pumping current) which is ½ of (100Ω×pumping current).

Such unsuccessful correction is caused by oscillation. In a range of not less than (50Ω×pumping current), the control system suffers an oscillation phenomenon, making it impossible to perform control.

In Japanese Utility Model Publication No. 7-45004, in order to measure the impedance of the oxygen pump, an amount corresponding to an alternating current (500 to 100 kHz) is superimposed on the power source so that the impedance of the oxygen pump is measured by using the alternating current voltage. However, oscillation tends to occur because the amount corresponding to the alternating current is subjected to positive feedback. For this reason, the output of the operational amplifier OP is subjected to positive feedback by the aid of a low pass filter so that the amount corresponding to the alternating current is eliminated. Thus only an amount corresponding to a direct current (for correcting voltage drop) is subjected to positive feedback, and an amount of voltage drop is superimposed on the pumping voltage Vp. In an experiment, the alternating current has a frequency of 10 kHz, and the low pass filter has a cut-off frequency of 1 kHz. In this system, the heater is not controlled on the basis of a signal of the amount corresponding to the alternating current.

According to the experiment, the oscillation phenomenon caused by the direct current component occurs at an extremely low frequency of not more than 50 Hz. Therefore, a problem of possible occurrence of oscillation due to the amount corresponding to the direct current still remains for the low pass filter which makes cutting for those having a frequency of not less than several hundreds Hz.

Further, this system requires an electric circuit comprising the low pass filter or the low pass filter+CR filter. It has been demanded to realize a simple system having a sufficient effect.

On the other hand, an all-range type oxygen sensor based on the use of an accurate oxygen pump is widely known as shown in FIG. 22. This oxygen sensor is formed with an internal space 124 for a pumping cell 120 and a sensor cell 122, and the internal space 124 communicates with an atmosphere of measurement gas via a diffusion rate-determining section 126.

Further, a sensor for measuring NOx is known, with which a gas (for example, NOx) including bound oxygen is measured by lowering the oxygen concentration in the gas to a constant low level by using an oxygen pump, and then further lowering the oxygen concentration to decompose NOx so that oxygen produced during the decomposition is measured by using an oxygen pump.

Such a sensor is provided with an oxygen concentration controller based on the use of the oxygen pump so that the oxygen concentration is controlled to be constant and low by using the oxygen concentration controller. Therefore, the oxygen concentration controller is required to have an accuracy which is equivalent to or higher than that of the oxygen sensor.

As for the all-range sensor, the pumping current is small in a range in which the oxygen concentration is low. Therefore, the accuracy is not lowered so much in such a range by the amount corresponding to voltage drop resulting from the impedance of the pump. On the other hand, in a range in which the oxygen concentration is high (for example several %), the accuracy is lowered due to the increased influence of the amount corresponding to voltage drop. However, no serious problem occurs even when an error is several hundreds ppm, because the oxygen concentration to be measured is several % (several ten thousands ppm).

On the contrary, for example, in the case of the NOx sensor which is used to measure the concentration of several thousands ppm at most, the change in oxygen concentration of the degree of several hundreds ppm brings about a large factor of error. Therefore, the oxygen concentration controller used for such a gas sensor is required to have a high degree of control accuracy.

As shown in FIG. 22, in the case of the oxygen sensor in which the oxygen concentration is controlled on the basis of an electromotive force generated between a measuring electrode 128 and a reference electrode 130, the pumping voltage (direct current voltage) Vp is subjected to feedback control so that a constant terminal voltage generated between the measuring electrode 128 and the reference electrode 130 is maintained. The oxygen sensor shown in FIG. 22 has a high degree of accuracy, however, it has a drawback that the control system suffers the oscillation phenomenon.

Namely, the feedback control is performed as follows. In general, a reference voltage as a target is compared by a comparator with the electromotive force generated between the measuring electrode 128 and the reference electrode 130. A difference obtained by the comparator is amplified to generate an amplified voltage on the basis of the difference from the target value. The amplified voltage is applied to the oxygen pump 132.

However, this system has a drawback that if the gain of the amplifier is set to be excessively large, the feedback control suffers oscillation.

This phenomenon is caused by the existence of any geometrical dimension of the measuring electrode 128 and the pumping electrode 134 contacting with the internal space 124. For example, when the oxygen concentration around the measuring electrode 128 is lower than the target value, the feedback control is performed so that the pumping voltage Vp is increased. Accordingly, the pumping voltage Vp is increased, the oxygen in the internal space 124 is pumped out, and the oxygen concentration in the internal space 124 is gradually decreased. However, the decrease in oxygen concentration is transmitted to a part of the space used for the measurement in a delayed manner due to the presence of the geometrical dimension described above. As a result, the oxygen concentration in the internal space 124 becomes lower than the target value. The lower oxygen concentration is detected by the measuring electrode 128 after a short delay period, and then the feedback control is performed so that the pumping voltage Vp is decreased.

In this case, the partial pressure of oxygen in the internal space 124 is gradually increased as well. However, a phenomenon occurs due to the geometrical dimension, in which the oxygen concentration in the internal space 124 has been excessively increased when the measuring electrode 128 detects the increase. As a result, the feedback control circuit suffers oscillation.

SUMMARY OF THE INVENTION

The present invention has been made taking the foregoing problems into consideration, an object of which is to provide a gas sensor and a gas concentration controller which make it possible to effectively avoid the oscillation phenomenon of a feedback control system for a control voltage supplied to an oxygen pump, for example, when the oxygen pump is used, and absorb the error in the amount corresponding to voltage drop resulting from the impedance of the oxygen pump so that the oxygen concentration can be accurately detected.

In order to achieve the object described above, the present invention provides a gas sensor comprising a first space surrounded by substrates composed of solid electrolytes, for introducing a measurement gas thereinto; a gas-pumping means including inner and outer electrodes formed inside and outside the first space surrounded by the substrates respectively, the substrate interposed by the both electrodes, and a pumping power source for applying, between the both electrodes, a control voltage for pumping out a predetermined gas component; a second space surrounded by substrates composed of solid electrolytes, for introducing a reference gas thereinto; a measuring means for measuring a terminal voltage between a reference electrode formed on the substrate and disposed on a side of the second space and the inner electrode of the gas-pumping means; a first control voltage-adjusting means for adjusting a level of the control voltage on the basis of the terminal voltage; a second control voltage-adjusting means for detecting a current flowing through the gas-pumping means when the gas component is pumped out by the gas-pumping means, and reflecting an obtained value of the current in the adjustment for the level of the control voltage performed by the first control voltage-adjusting means; and a spike-suppressing means for suppressing a spike signal generated in the second control voltage-adjusting means.

According to the present invention, at first, the measurement gas is introduced into the first space. At this time, the measuring means is operated to measure the terminal voltage between the inner electrode of the gas-pumping means and the reference electrode formed on the side of the second space. The measured voltage is supplied to the first control voltage-adjusting means. The first control voltage-adjusting means adjusts the level of the control voltage to be supplied to the gas-pumping means, on the basis of the measured voltage. The gas-pumping means pumps out an amount of the predetermined gas component contained in the measurement gas introduced into the first space, the amount corresponding to the level of the control voltage. The supply of the level-adjusted control voltage to the gas-pumping means allows the concentration of the predetermined gas component in the first space to be subjected to feedback control so that a predetermined level is achieved.

In the present invention, the measured voltage measured by the measuring means to be utilized for adjusting the level of the control voltage is the terminal voltage between the inner electrode of the gas-pumping means and the reference electrode disposed in the second space. Accordingly, when the amount of the predetermined gas component pumped out by the gas-pumping means is changed, and the concentration of the gas component is changed in the first space, then the terminal voltage between the inner electrode of the gas-pumping means and the reference electrode is changed without any time delay. Therefore, the oscillation phenomenon in the feedback control is suppressed.

The current flows through the gas pump when the predetermined gas component is pumped out by the gas-pumping means. Therefore, the amount corresponding to voltage drop resulting from the impedance of a gas pump appears as an error for the level adjustment for the control voltage. However, according to the present invention, the current flowing through the gas-pumping means is detected by the second control voltage-adjusting means, and the value of the detected current is reflected in the level adjustment in the first control voltage-adjusting means. Therefore, the error is effectively absorbed, making it possible to accurately perform the feedback control for the gas-pumping means. Thus the concentration of the predetermined gas component contained in the measurement gas introduced into the first space can be detected with a high degree of accuracy.

When the control voltage is changed, for example, in a step-forming manner, in accordance with the adjusting operation performed by the first control voltage-adjusting means, a large current instantaneously flows through the gas-pumping means. As a result, a spike-shaped noise is generated in the second control voltage-adjusting means in some cases. When the second control voltage-adjusting means is arranged as a positive feedback type adjusting circuit, it is feared that oscillation may be caused by the spike-shaped noise.

However, the present invention is provided with the spike-suppressing means for suppressing the spike signal generated in the second control voltage-adjusting means. Accordingly, the spike-shaped noise can be effectively suppressed, making it possible to avoid the oscillation in the second control voltage-adjusting means. This results in highly accurate adjustment for the control voltage, performed by the first control voltage-adjusting means. Thus it is possible to highly accurately measure the concentration of the predetermined gas component contained in the measurement gas introduced into the first space.

In one embodiment of the present invention constructed as described above, it is preferable that the first control voltage-adjusting means is provided with a comparing means for determining a deviation between the terminal voltage and a comparative voltage, and the level of the control voltage is adjusted on the basis of the deviation obtained by the comparing means. In this embodiment, the control voltage is subjected to feedback control so that the terminal voltage converges to the comparative voltage.

In another embodiment of the present invention constructed as described above, it is preferable that the second control voltage-adjusting means is provided with a resistor for detecting the current flowing through the gas-pumping means and converting the current into a voltage when the gas component is pumped out by the gas-pumping means, and an amplifier for amplifying the terminal voltage of the resistor with a predetermined gain and superimposing an obtained voltage on the comparative voltage. Accordingly, the current, which is generated when the predetermined gas component is pumped out by the gas-pumping means, flows through the resistor. As a result, a voltage drop occurs in the resistor. The voltage of the amount corresponding to the voltage drop is amplified by the amplifier with the predetermined gain, and the obtained voltage is superimposed on the comparative voltage in the first control voltage-adjusting means. Namely, the amount corresponding to the voltage drop resulting from the impedance of the gas-pumping means is reflected in the adjustment for the control voltage operated in the first control voltage-adjusting means. Thus the error based on the impedance of the gas-pumping means is effectively absorbed, making it possible to accurately perform the feedback control.

In still another embodiment, it is preferable that the spike-suppressing means is provided with a capacitor connected to both ends of the resistor. In this embodiment, the resistor and the capacitor provide a time constant which realizes an arrangement in which a phase-compensating circuit for proportional integral operation is inserted and connected to the feedback control system. Thus it is possible to effectively suppress the spike-shaped noise generated in the second control voltage-adjusting means.

Alternatively, it is preferable that the spike-suppressing means is provided with a capacitor connected between the resistor and the amplifier, or the spike-suppressing means is provided with a capacitor connected between the amplifier and a generating source of the comparative voltage.

In still another embodiment of the present invention as described above, it is preferable that a gas diffusion rate-determining section for giving a predetermined diffusion resistance to the measurement gas is provided at a passage for introducing the measurement gas into the first space. In still another embodiment, it is preferable that the gas sensor further comprises a third space for introducing the measurement gas in the first space thereinto; a second gas diffusion-rate determining section provided at a passage for introducing the measurement gas into the third space, for giving a predetermined diffusion resistance to the measurement gas; a measurement gas-decomposing means disposed in the third space, for decomposing and degrading the predetermined gas component in the measurement gas; and a gas component-detecting means for detecting the predetermined gas component decomposed and degraded by the measurement gas-decomposing means. Alternatively, it is preferable that the gas sensor further comprises a gas component supply means for feeding the predetermined gas component to the third space; and a gas component-detecting means for detecting the gas component fed by the gas component supply means. In this embodiment, the amount of the predetermined gas component contained in the measurement gas can be effectively controlled, making it possible to measure, for example, the amount of oxides or inflammable gases contained in the measurement gas with a high degree of accuracy.

According to another aspect of the present invention, there is provided a gas concentration controller comprising a first space surrounded by substrates composed of solid electrolytes, for introducing a measurement gas thereinto; a gas diffusion rate-determining section provided at a passage for introducing the measurement gas into the first space, for giving a predetermined diffusion resistance to the measurement gas; a gas-pumping means including inner and outer electrodes formed inside and outside the first space surrounded by the substrates respectively, the substrate interposed by the both electrodes, and a pumping power source for applying, between the both electrodes, a control voltage for pumping out a predetermined gas component; a second space surrounded by substrates composed of solid electrolytes, for introducing a reference gas thereinto; a measuring means for measuring a terminal voltage between a reference electrode formed on the substrate and disposed on a side of the second space and the inner electrode of the gas-pumping means; a first control voltage-adjusting means for adjusting a level of the control voltage on the basis of the terminal voltage; a second control voltage-adjusting means for detecting a current flowing through the gas-pumping means when the gas component is pumped out by the gas-pumping means, and reflecting an obtained value of the current in the adjustment for the level of the control voltage performed by the first control voltage-adjusting means; and a spike-suppressing means for suppressing a spike signal generated in the second control voltage-adjusting means.

According to the present invention, at first, the measurement gas is introduced into the first space via the gas diffusion rate-determining means. At this time, the measuring means is operated to measure the terminal voltage between the inner electrode of the gas-pumping means and the reference electrode formed on the side of the second space. The measured voltage is supplied to the first control voltage-adjusting means. The first control voltage-adjusting means adjusts the level of the control voltage to be supplied to the gas-pumping means, on the basis of the measured voltage. The gas-pumping means pumps out an amount of the predetermined gas component contained in the measurement gas introduced into the first space, the amount corresponding to the level of the control voltage. The supply of the level-adjusted control voltage to the gas-pumping means allows the concentration of the predetermined gas component in the first space to be subjected to feedback control so that a predetermined level is achieved.

In the present invention, the measured voltage measured by the measuring means to be utilized for adjusting the level of the control voltage is the terminal voltage between the inner electrode of the gas-pumping means and the reference electrode disposed in the second space. Accordingly, when the amount of the predetermined gas component pumped out by the gas-pumping means is changed, and the concentration of the gas component is changed in the first space, then the terminal voltage between the inner electrode of the gas-pumping means and the reference electrode is changed without any time delay. Therefore, the oscillation phenomenon in the feedback control is suppressed.

The current flows through the gas pump when the predetermined gas component is pumped out by the gas-pumping means. Therefore, the amount corresponding to voltage drop resulting from the impedance of the gas pump appears as an error for the level adjustment for the control voltage. However, according to the present invention, the current flowing through the gas-pumping means is detected by the second control voltage-adjusting means, and the value of the detected current is reflected in the level adjustment in the first control voltage-adjusting means. Therefore, the error is effectively absorbed, making it possible to accurately perform the feedback control for the gas-pumping means. Thus the concentration of the predetermined gas component contained in the measurement gas introduced into the first space can be detected with a high degree of accuracy.

When the control voltage is changed, for example, in a step-forming manner, in accordance with the adjusting operation performed by the first control voltage-adjusting means, a large current instantaneously flows through the gas-pumping means. As a result, a spike-shaped noise is generated in the second control voltage-adjusting means in some cases. When the second control voltage-adjusting means is arranged as a positive feedback type adjusting circuit, it is feared that oscillation may be caused by the spike-shaped noise.

However, the present invention is provided with the spike-suppressing means for suppressing the spike signal generated in the second control voltage-adjusting means. Accordingly, the spike-shaped noise can be effectively suppressed, making it possible to avoid the oscillation in the second control voltage-adjusting means. This results in highly accurate adjustment for the control voltage, performed by the first control voltage-adjusting means. Thus it is possible to highly accurately measure the concentration of the predetermined gas component contained in the measurement gas introduced into the first space.

In one embodiment of the present invention constructed as described above, it is preferable that the first control voltage-adjusting means is provided with a comparing means for determining a deviation between the terminal voltage and a comparative voltage, and the level of the control voltage is adjusted on the basis of the deviation obtained by the comparing means. In this embodiment, the control voltage is subjected to feedback control so that the terminal voltage converges to the comparative voltage.

In another embodiment of the present invention constructed as described above, it is preferable that the second control voltage-adjusting means is provided with a resistor for detecting the current flowing through the gas-pumping means and converting the current into a voltage when the gas component is pumped out by the gas-pumping means, and an amplifier for amplifying the terminal voltage of the resistor with a predetermined gain and superimposing an obtained voltage on the comparative voltage. Accordingly, the current, which is generated when the predetermined gas component is pumped out by the gas-pumping means, flows through the resistor. As a result, a voltage drop occurs in the resistor. The voltage of the amount corresponding to the voltage drop is amplified by the amplifier with the predetermined gain, and the obtained voltage is superimposed on the comparative voltage in the first control voltage-adjusting means. Namely, the amount corresponding to the voltage drop resulting from the impedance of the gas-pumping means is reflected in the adjustment for the control voltage operated in the first control voltage-adjusting means. Thus the error based on the impedance of the gas-pumping means is effectively absorbed, making it possible to accurately perform the feedback control.

In still another embodiment, it is preferable that the spike-suppressing means is provided with a capacitor connected to both ends of the resistor. In this embodiment, the resistor and the capacitor provide a time constant which realizes an arrangement in which a phase-compensating circuit for proportional integral operation is inserted and connected to the feedback control system. Thus it is possible to effectively suppress the spike-shaped noise generated in the second control voltage-adjusting means.

Alternatively, it is preferable that the spike-suppressing means is provided with a capacitor connected between the resistor and the amplifier, or or the spike-suppressing means is provided with a capacitor connected between the amplifier and a generating source of the comparative voltage.

The above and other objects, features and advantages of the present invention will become more apparent from the following description when taken in conjunction with the accompanying drawings in which a preferred embodiment of the present invention is shown by way of illustrative example.

DESCRIPTION OF THE DRAWINGS

FIG. 5A shows a waveform obtained when the pumping voltage is changed in a step-forming manner.

FIG. 5B shows a waveform illustrating the change in pumping current, obtained when the pumping voltage is changed in a step-forming manner.

FIG. 5C shows a waveform illustrating a situation in which a spike-shaped noise is generated in the correction volt age when the pumping voltage is changed in a step-forming manner.

DESCRIPTION OF THE PREFERRED EMBODIMENTS

Explanation will be made below with reference to FIGS. 1 to 16 for two illustrative embodiments in which the gas sensor according to the present invention is applied to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm (hereinafter simply referred to as "gas sensor according to the first embodiment" and "gas sensor according to the second embodiment" respectively).

At first, before explaining the gas sensor according to the embodiment of the present invention, explanation will be made for an arrangement of a gas sensor (hereinafter conveniently referred to as "gas sensor constructed for the purpose of comparison") produced before getting the idea of the gas sensor according to the present invention.

Figure 1:
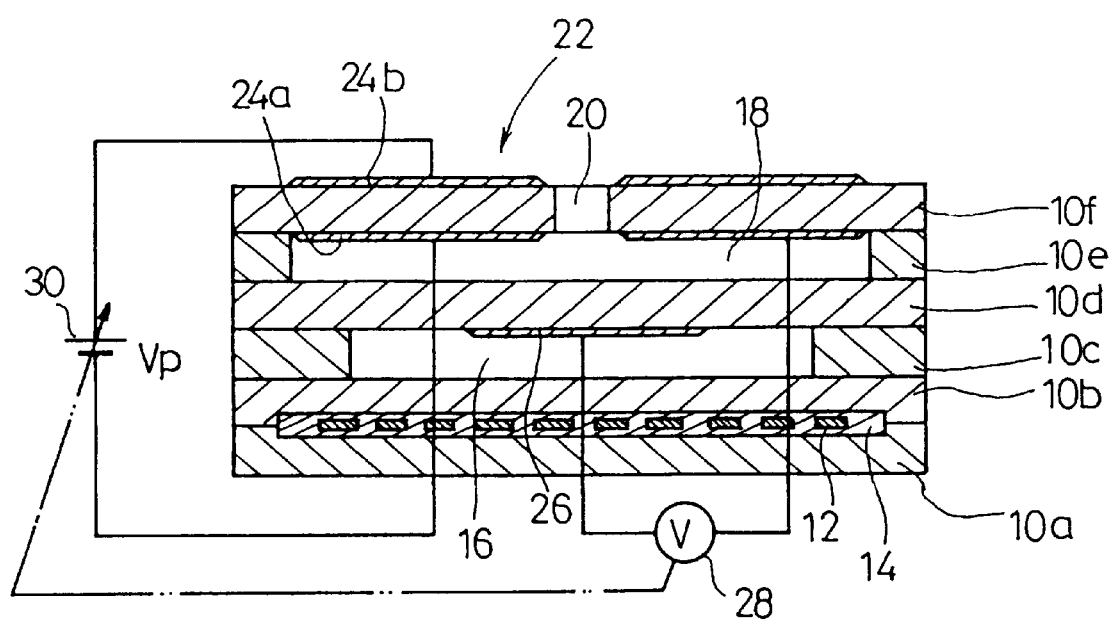
FIG. 1 shows a schematic arrangement of a gas sensor (hereinafter simply referred to as "gas sensor constructed for the purpose of comparison") produced before getting an idea of a gas sensor according to the present invention.

As shown in FIG. 1, the gas sensor constructed for the purpose of comparison comprises, for example, six stacked solid electrolyte layers 10a to 10f composed of ceramics based on the use of oxygen ion-conductive solid electrolytes such as $ZrO_2$. First and second layers from the bottom are designated as first and second substrate layers 10a, 10b respectively. Third and fifth layers from the bottom are designated as first and second spacer layers 10c, 10e respectively. Fourth and sixth layers from the bottom are designated as first and second solid electrolyte layers 10d, 10f respectively.

Specifically, the first spacer layer 10c is stacked on the second substrate layer 10b. The first solid electrolyte layer 10d, the second spacer layer 10e, and the second solid electrolyte layer 10f are successively stacked on the first spacer layer 10c. A heater 12 for enhancing the oxygen ion conductivity is embedded through an insulative film 14 between the first and second substrate layers 10a, 10b.

A space (reference gas-introducing space) 16, into which a reference gas such as atmospheric air to be used as a reference for measuring oxides is introduced, is formed between the second substrate layer 10b and the first solid electrolyte layer 10d, the space 16 being comparted by a lower surface of the first solid electrolyte layer 10d, an upper surface of the second substrate layer 10b, and side surfaces of the first spacer layer 10c.

A space (gas-introducing space) 18, into which a measurement gas is introduced, is formed between the first and second solid electrolyte layers 10d, 10f, the space 18 being comparted by a lower surface of the second solid electrolyte layer 10f, an upper surface of the first electrolyte layer 10d, and side surfaces of the second spacer layer 10e. A diffusion rate-determining section 20, which communicates with the gas-introducing space 18, is formed through the uppermost second solid electrolyte layer 10f. The diffusion rate-determining section 20 is provided for giving a predetermined diffusion resistance to the measurement gas to be introduced into the gas-introducing space 18. The diffusion-rate determining section 20 can be formed as a passage composed of, for example, a porous material, or a small hole having a predetermined cross-sectional area so that the measurement gas may be introduced.

A first electrode (inner pumping electrode 24a) for constructing an oxygen pump 22 as described later on is formed on a portion of the lower surface of the second solid electrolyte layer 10f for forming the gas-introducing space 18. A second electrode (outer pumping electrode 24b) for constructing the oxygen pump 22 is formed on the upper surface of the second solid electrolyte layer 10f.

A reference electrode 26 for measuring the partial pressure of oxygen contained in the measurement gas is formed on a portion of the lower surface of the first solid electrolyte layer 10d for forming the reference gas-introducing space 16.

In this arrangement, an electromotive force of an oxygen concentration cell is generated on the basis of a difference between a partial pressure of oxygen in the atmospheric air introduced into the reference gas-introducing space 16 and a partial pressure of oxygen in the measurement gas introduced into the gas-introducing space 18. The electromotive force is represented by an electric potential difference V between the reference gas-introducing space 16 and the gas-introducing space 18. The electric potential difference V can be determined in accordance with the following Nernst's equation.

$$V = RT/4F \cdot \ln(P_1(O_2)/P_0(O_2))$$

R: gas constant;
T: absolute temperature;
F: Faraday constant;
$P_1(O_2)$: partial pressure of oxygen in the gas-introducing space;
$P_0(O_2)$: partial pressure of oxygen in the reference gas.

Therefore, the partial pressure of oxygen in the gas-introducing space 18 can be detected by measuring the electric potential difference V generated on the basis of the Nernst's equation, by using a potentiometer 28.

The inner pumping electrode 24a and the outer pumping electrode 24b, which are formed on the inner and outer surfaces of the second solid electrolyte layer 10f respectively, construct the oxygen pump 22 for setting the partial pressure of oxygen in the measurement gas introduced into the gas-introducing space 18 to have a predetermined value. Namely, the solid electrolyte layer, which is composed of a material such as $ZrO_2$ provided with the oxygen ion conductivity, functions as a pump for pumping out oxygen upon application of a voltage. The both pumping electrodes 24a, 24b construct a voltage-applying means for allowing the solid electrolyte layer to perform the pumping operation.

In general, a pumping voltage Vp, which is set on the basis of the electric potential difference V detected by the potentiometer 28, is applied between the inner pumping electrode 24a and the outer pumping electrode 24b by the aid of a variable power source 30. Oxygen is pumped out from or pumped in into the gas-introducing space 18 by the oxygen pump 22 in accordance with application of the pumping voltage Vp. Accordingly, the partial pressure of oxygen in the gas-introducing space 18 is set to have a predetermined value.

The gas sensor constructed for the purpose of comparison is arranged such that the voltage between the inner pumping electrode 24a and the reference electrode 26 is measured to determine a difference between the measured voltage and the reference voltage so that the pumping voltage Vp is controlled on the basis of the determined difference in voltage or differential voltage.

Figure 2:
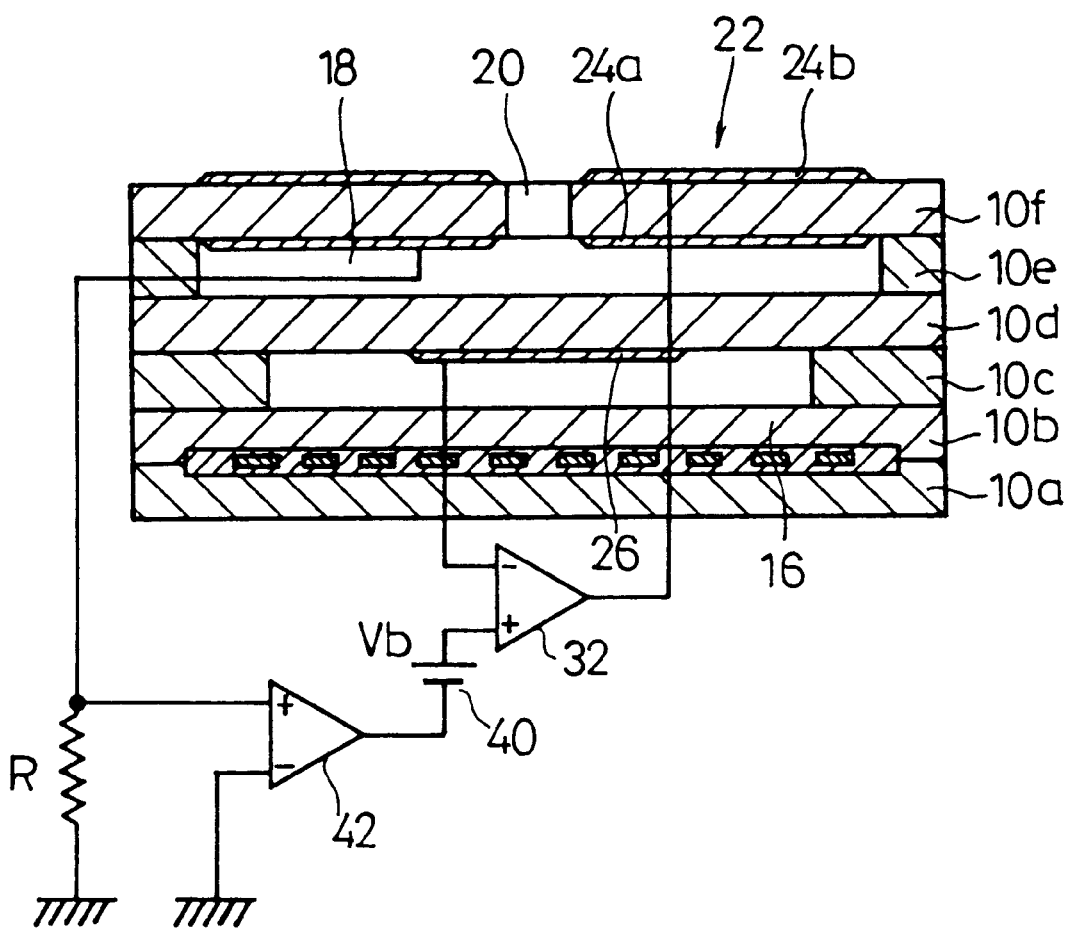
FIG. 2 shows a specified arrangement of the gas sensor constructed for the purpose of comparison.

Specifically, as shown in FIG. 2, the gas sensor constructed for the purpose of comparison is wired and connected as follows. Namely, the gas sensor is provided with a comparative amplifier 32 for comparing the reference voltage Vb with the terminal voltage between the reference electrode 26 and the inner pumping electrode 24 to obtain an amount corresponding to a difference therebetween, and amplifying the amount corresponding to the difference with a predetermined gain to make an output. The output voltage (differential voltage) from the comparative amplifier 32 is applied, as the pumping voltage Vp supplied to the oxygen pump 22, between the inner pumping electrode 24a and the outer pumping electrode 24b.

In this arrangement, when the amount of oxygen pumped out by the oxygen pump 22 is changed, and the oxygen concentration in the gas-introducing space 18 is changed, then the terminal voltage between the inner pumping electrode 24a of the oxygen pump 22 and the reference electrode 26 is changed without any time delay (the terminal voltage is changed in real-time). Accordingly, the oscillation phenomenon in the feedback control can be effectively suppressed.

In the feedback control system, the pumping voltage Vp (output voltage) is subjected to feedback control so that the terminal voltage between the inner pumping electrode 24a and the reference electrode 26 converges to the same level as that of the reference voltage Vb.

In addition to the arrangement described above, the gas sensor constructed for the purpose of comparison further comprises a resistor R connected between the inner pumping electrode 24a and GND, and an amplifier 42 (operational amplifier) inserted and connected between one end of the resistor R and a generating source (power source 40) of the reference voltage Vb. Specifically, the one end of the resistor R is connected to a non-inverting terminal of the amplifier 42, and an inverting terminal of the amplifier 42 is connected to the ground. An output terminal of the amplifier 42 is connected to a negative pole of the power source 40.

Namely, the gas sensor constructed for the purpose of comparison is wired and connected such that the current, which flows between the inner pumping electrode 24a and the outer pumping electrode 24b corresponding to the oxygen pumped out by the oxygen pump 22, is converted into a voltage corresponding to a value of the current in accordance with the voltage drop in the resistor R, and the voltage is applied to the non-inverting terminal of the amplifier 42.

In general, the current (pumping current) flows through the oxygen pump 22 when the oxygen is pumped out by the oxygen pump 22. Therefore, the amount corresponding to the voltage drop resulting from the impedance of the oxygen pump 22 appears as an error in the operation of level adjustment for the pumping voltage Vp.

However, in the gas sensor constructed for the purpose of comparison, the pumping current flowing through the oxygen pump 22 is converted into the voltage by using the resistor R, and the voltage is amplified by the amplifier 42 with a predetermined gain to obtain a correction voltage which is superimposed on the power source 40. Namely, only the amount corresponding to the voltage drop resulting from a boundary resistance (impedance) of the inner pumping electrode 24a is superimposed on the voltage between the inner pumping electrode 24a and the reference electrode 26. The amount corresponding to the voltage drop is considerably decreased. Therefore, it is sufficient for the amount corresponding to the voltage drop to be slightly corrected, and hence the accuracy is improved to that extent. In other words, the amount corresponding to the voltage drop resulting from the impedance of the oxygen pump 22 is reflected, as the correction voltage, in the reference voltage (or superimposed on the reference voltage). Accordingly, it is possible to effectively absorb the error resulting from the impedance of the oxygen pump 22 with respect to the pumping voltage Vp, making it possible to perform the feedback control for the pumping voltage Vp with a high degree of accuracy. This results in highly accurate detection of the oxygen concentration in the gas-introducing space 18.

In the gas sensor constructed for the purpose of comparison as described above, when the pumping current flowing between the outer pumping electrode 24b and the inner pumping electrode 24a of the oxygen pump 22 is increased, and the sum of (reference voltage+correction voltage) is increased, then positive feedback proceeds such that the output voltage of the comparative amplifier 32 is increased, and consequently the pumping current is increased, resulting in a state in which oscillation tends to occur. In fact, it has been revealed that it is impossible to correct a voltage corresponding to (impedance of oxygen pump 22×pumping current).

Figure 3:
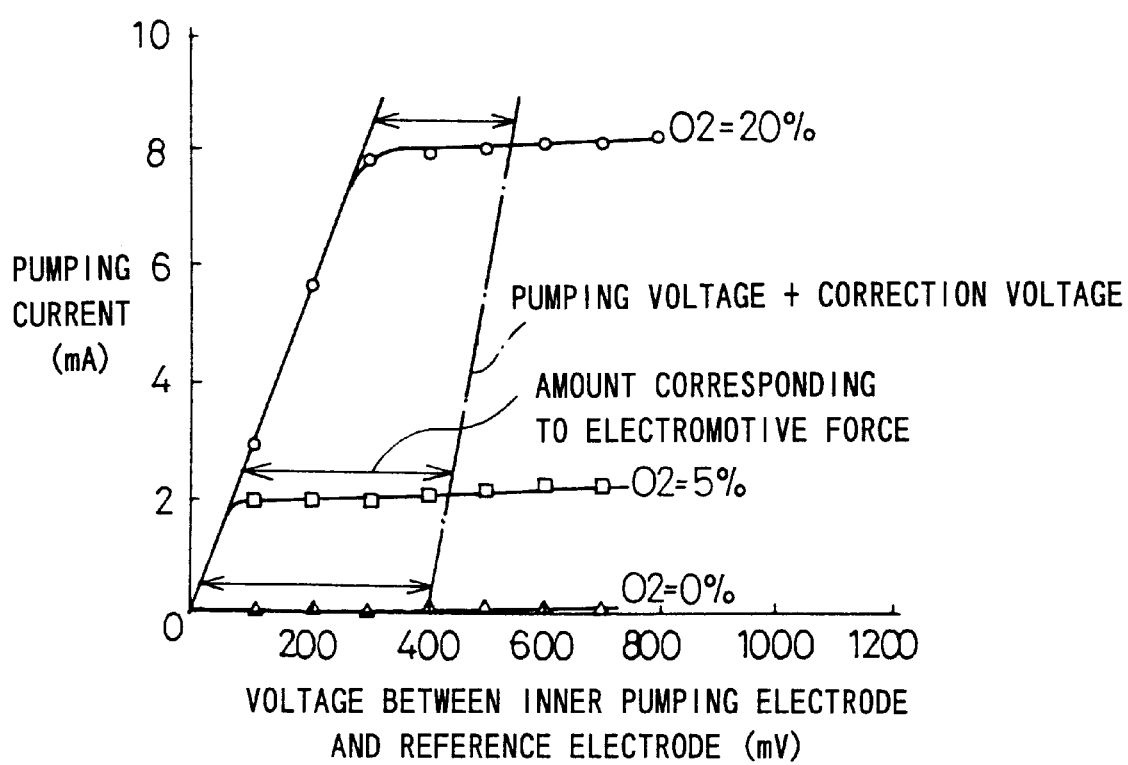
FIG. 3 shows a limiting current characteristic of the gas sensor constructed for the purpose of comparison.

FIG. 3 shows a characteristic illustrating such a state. In this experiment, the temperature of the oxygen pump 22 is adjusted so that the impedance of the oxygen pump 22 is 100Ω. On this condition, the impedance between the inner pumping electrode 24a and the reference electrode 26 is 35Ω, and an ideal value of the correction voltage is (35Ω× pumping current). However, in fact, correction is successful only for (17.5Ω×pumping current) which is ½ of the ideal value, due to oscillation.

Therefore, if the impedance of the oxygen pump 22 is increased during the course of use, the operation point possibly deviates from the flat portion of the limiting current characteristic.

The present invention has been made in order to solve the problem as described above, which makes it possible to perform correction for those equivalent to or not less than the amount of (impedance of oxygen pump 22×pumping current) by using simple electronic components without using an impedance-measuring means, a heater control means based thereon, and a correction voltage control means. Further, the present invention makes is possible to perform operation at the flat portion of the limiting current characteristic even when the impedance of the oxygen pump 22 is increased during the course of use.

Figure 4:
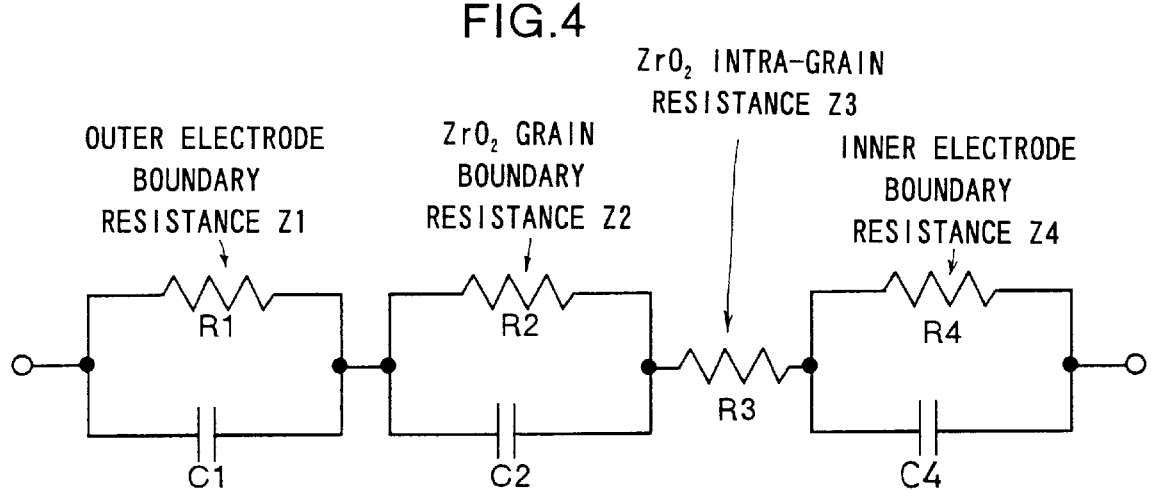
FIG. 4 shows an equivalent circuit illustrating an impedance of an oxygen pump.

The oscillation phenomenon does not simply results from the positive feedback only. The oscillation phenomenon also results from the fact that the impedance of the oxygen pump 22 is constructed as shown in FIG. 4, and it contains a large amount of capacitance components. Namely, the impedance of the oxygen pump 22 is equivalent to a circuit comprising a boundary resistance Z1 between the outer pumping electrode 24 and the second solid electrolyte layer 10f, based on parallel connection of a resistance R1 and a capacitance C1; a grain boundary resistance Z2 between $ZrO_2$ grains in the second solid electrolyte layer 10f, based on parallel connection of a resistance R2 and a capacitance C2; a $ZrO_2$ grain resistance Z3 in the second solid electrolyte layer 10f, based on the resistor R; and a boundary resistance Z4 between the inner pumping electrode 24a and the second solid electrolyte layer 10f, based on parallel connection of a resistance R4 and a capacitance C4, the resistances Z1 to Z4 being connected in series. Therefore, the impedance of the oxygen pump 22 contains a large amount of the capacitance components.

Therefore, as shown in FIG. 5A, for example, when the pumping voltage is quickly raised in a step-forming manner, the pumping current instantaneously flows through the resistance R3 and the capacitance C4 via the capacitance C1 and the capacitance C2. The resistance R1, the resistance R2, and the resistance R4 are neglected. Therefore, a large current flows as shown in FIG. 5B. If the pumping voltage is maintained, the capacitance C1, the capacitance C2, and the capacitance C4 are charged along with the passage of time. Consequently, the current is settled to be a value determined by resistance R1+resistance R2+resistance R3+resistance R4.

Namely, as shown in FIG. 5C, the correction voltage, which is superimposed on the reference voltage Vb, instantaneously becomes a large voltage, and it is settled to be a certain constant value in accordance with settlement of the current. The spike of the pumping current, and the resultant spike of the correction voltage quickly increase the positive feedback voltage in the amplifier 42. As a result, it is feared that oscillation may occur.

In the present invention, the spike of the pumping current is suppressed so that the occurrence of the oscillation phenomenon is suppressed, the correctable region (correctable dynamic range) is enlarged, and the decrease in accuracy, which would be otherwise caused by the increase in impedance of the oxygen pump 22 during the course of use, is improved.

Next, a gas sensor according to the first embodiment of the present invention will be explained with reference to FIGS. 6 to 11. Components or parts corresponding to those shown in FIG. 1 are designated by identical reference numerals.

The gas sensor according to the first embodiment is constructed in approximately the same manner as the gas sensor constructed for the purpose of comparison described above. However, the gas sensor according to the first embodiment is different from the gas sensor constructed for the purpose of comparison in the following points. Namely, a resistor Ri for detecting the pumping current is inserted and connected between the output terminal of the comparative amplifier 32 and the outer pumping electrode 24b of the oxygen pump 22. Both ends of the resistor Ri form a short circuit with a capacitor C inserted therebetween. Further, one electrode of the capacitor C is connected to a non-inverting terminal of a differential amplifier 44, and the other electrode of the capacitor C is connected to an inverting terminal of the differential amplifier 44.

In the gas sensor according to this embodiment, the resistor Ri and the capacitor C provide a time constant which realizes an arrangement in which a phase-compensating circuit for proportional integral operation is inserted and connected to the feedback control system for the pumping voltage Vp. Thus it is possible to effectively suppress the spike-shaped noise generated in the output voltage of the differential amplifier 44, i.e., in the correction voltage.

For example, when the pumping current is raised to a high level, the capacitor C is charged with the current corresponding to the raised portion. However, in this embodiment, the capacitor C is firstly charged with the current corresponding to the spike-shaped portion of the pumping current. Therefore, the waveform of the voltage applied to the differential amplifier 44 located downstream is a substantially rectangular signal waveform. Namely, the spike-shaped noise in the pumping current is suppressed by the capacitor C. As a result, the spike-shaped noise in the correction voltage to be superimposed on the reference voltage is also suppressed. This results in high accuracy of the adjustment for the pumping voltage Vp, performed by the comparative amplifier 32. Accordingly, it is possible to accurately measure the oxygen concentration in the measurement gas introduced into the gas-introducing space 18.

Figure 7:
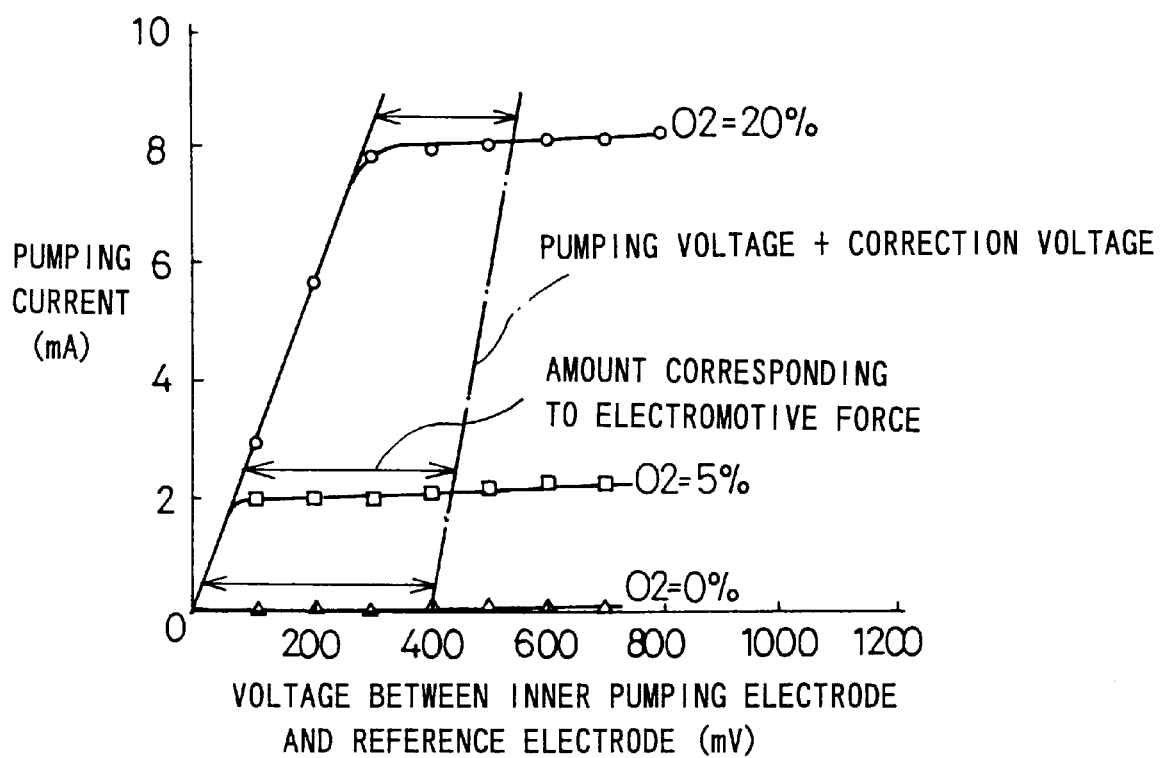
FIG. 7 shows a limiting current characteristic of the gas sensor constructed for the purpose of comparison.
Figure 8:
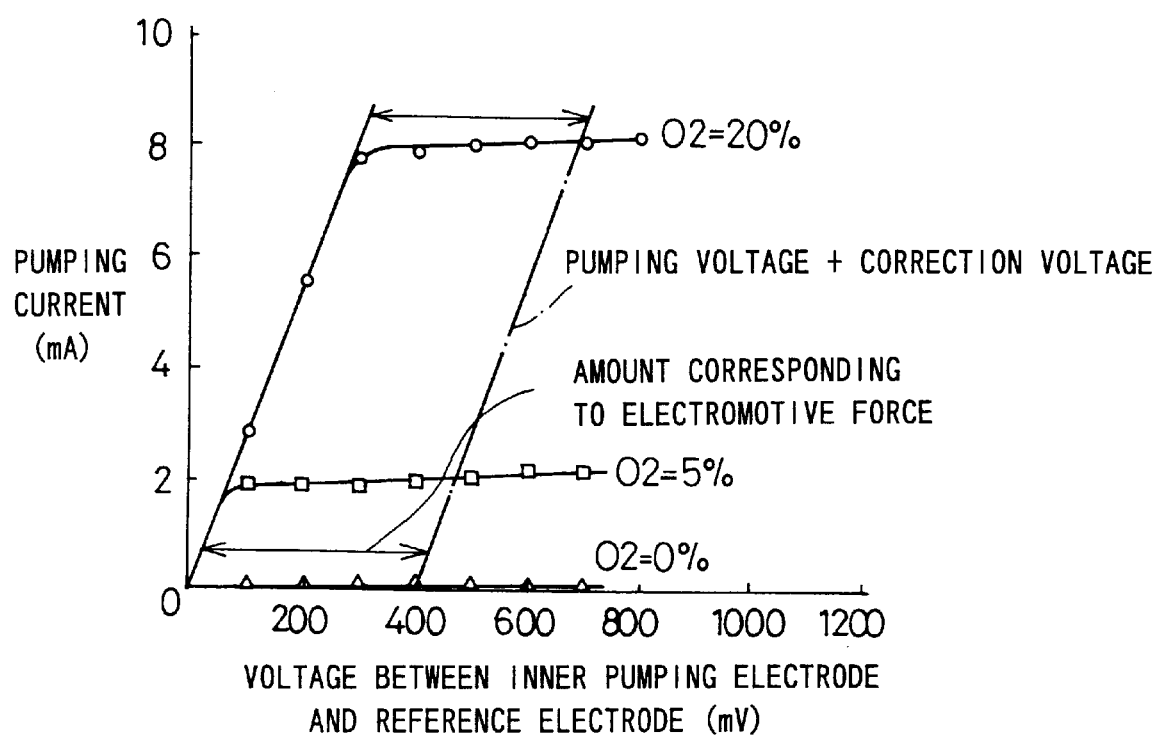
FIG. 8 shows a limiting current characteristic of the gas sensor according to the embodiment of the present invention.

Now, explanation will be made for an experiment concerning limiting current characteristics of the gas sensor according to the embodiment of the present invention (working example) and the gas sensor constructed for the purpose of comparison (comparative example). FIG. 7 shows the limiting current characteristic obtained for the comparative example in this experiment, and FIG. 8 shows the limiting current characteristic obtained for the working example. In this experiment, heating is performed so that the oxygen pump 22 has an impedance of 100Ω. On this condition, the impedance between the inner pumping electrode 24a and the reference electrode 26 is 35Ω, and an ideal value of the correction voltage is (35Ω×pumping current). In order to simplify the experiment, the amplification degree of the differential amplifier 44 is considered to be 1.

Figure 21:
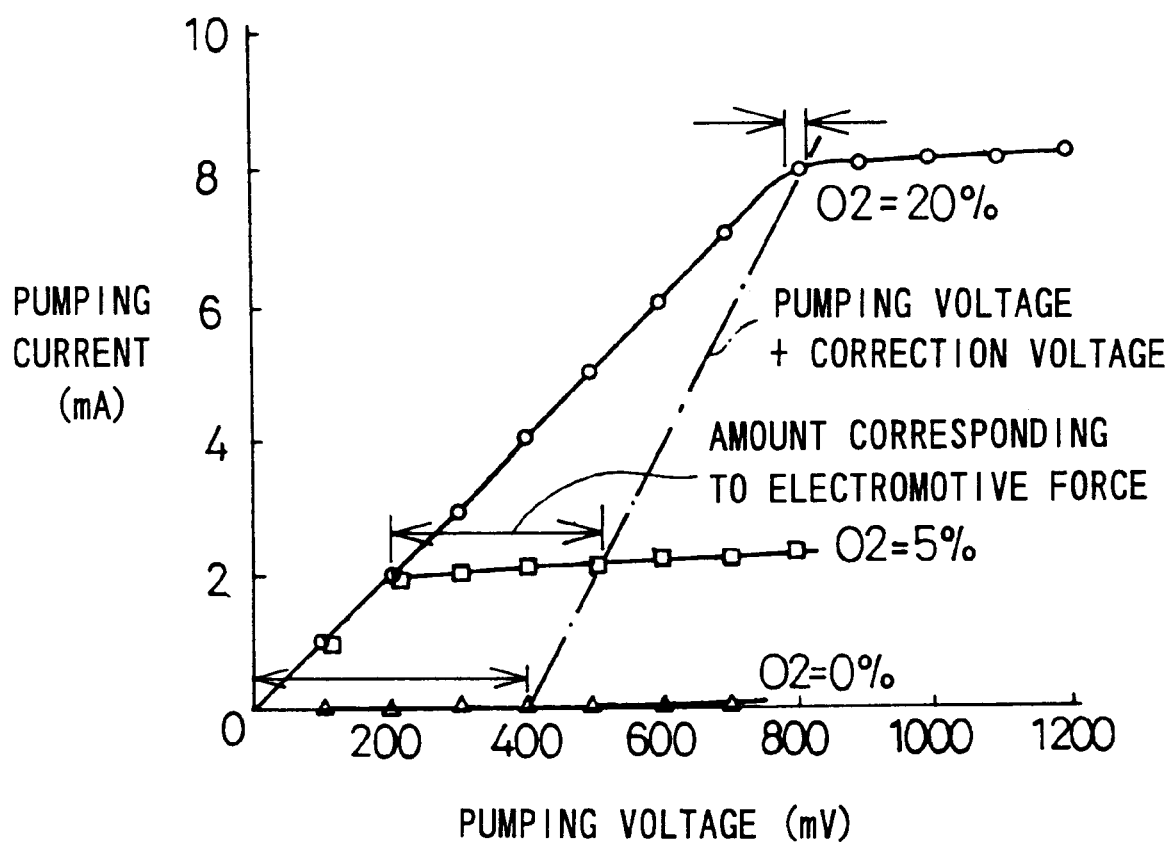
FIG. 21 shows a limiting current characteristic obtained when the oxygen pump is used as an oxygen concentration controller.
Figure 22:
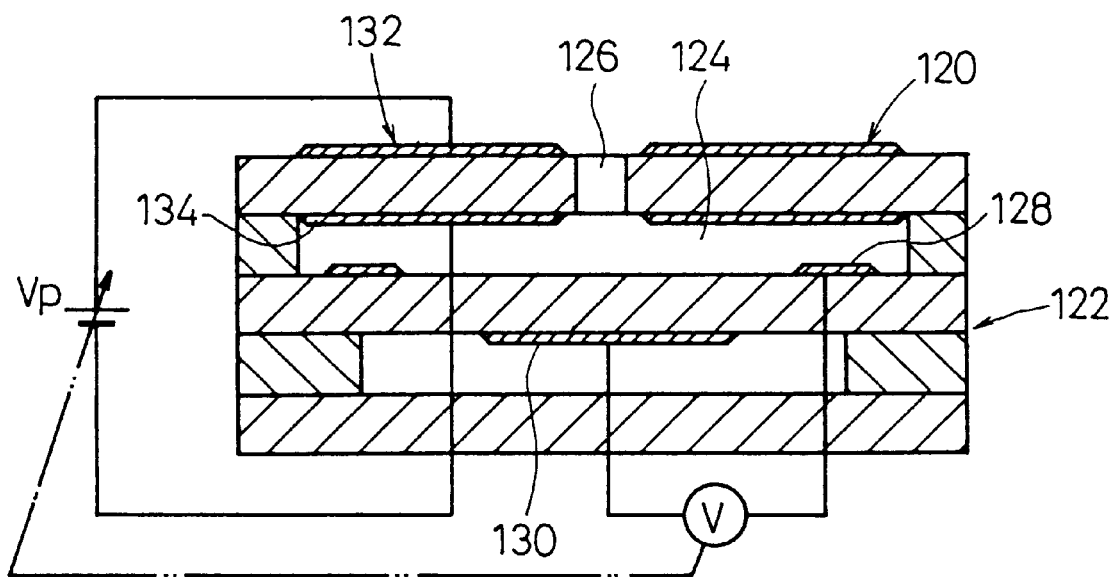
FIG. 22 shows an arrangement of a conventional all-range type oxygen sensor based on the use of the oxygen pump.

In the case of the comparative example, oscillation occurs if the resistor R has a resistance value of not less than 18Ω. Accordingly, the resistance value is set to be 17.5Ω which is ½ of the ideal value 35Ω. Therefore, the amount of correction is ½ of the ideal value. However, it is understood that the amount of correction is greatly improved as compared with the conventional gas sensor (see the characteristic curve shown in FIG. 21). This is because of the following effect. Namely, in the case of the conventional gas sensor, it is necessary to correct all of the impedance Zp of the oxygen pump 22. On the contrary, in the case of the comparative example and the working example, Z1, Z2, and Z3 in the following expression can be neglected for controlling the pumping voltage Vp based on the voltage between the inner pumping electrode 24a and the reference electrode 26. Therefore, the amount corresponding to the voltage drop to be corrected is greatly decreased.

$$Zp=Z1+Z2+Z3+Z4$$

Z1: boundary resistance between the outer pumping electrode 24 and the second solid electrolyte layer 10f;

Z2: boundary resistance between $ZrO_2$ grains in the second solid electrolyte layer 10f;

Z3: $ZrO_2$ grain resistance in the second solid electrolyte layer 10f;

Z4: boundary resistance between the inner pumping electrode 24a and the second solid electrolyte layer 10f.

When the gas sensor is provided with the capacitor C (capacitor C has a capacitance of 300 μF), no oscillation occurs even when the resistance value of the resistor Ri for detecting the pumping current is set to be 35Ω. For this reason, the resistance value of the resistor Ri for detecting the pumping current is set to be 35Ω. However, it has been confirmed that the limit point for occurrence of oscillation is in the vicinity of 50Ω which is larger than the ideal value of 35Ω by about 50%.

As clarified from FIG. 8, when the gas sensor is provided with the capacitor C, it is possible to perform the ideal correction. The gas sensor can be operated while maintaining the operation point to be located on any of points concerning the identical amount corresponding to the electromotive force, even when the oxygen concentration is greatly changed.

Figure 9:
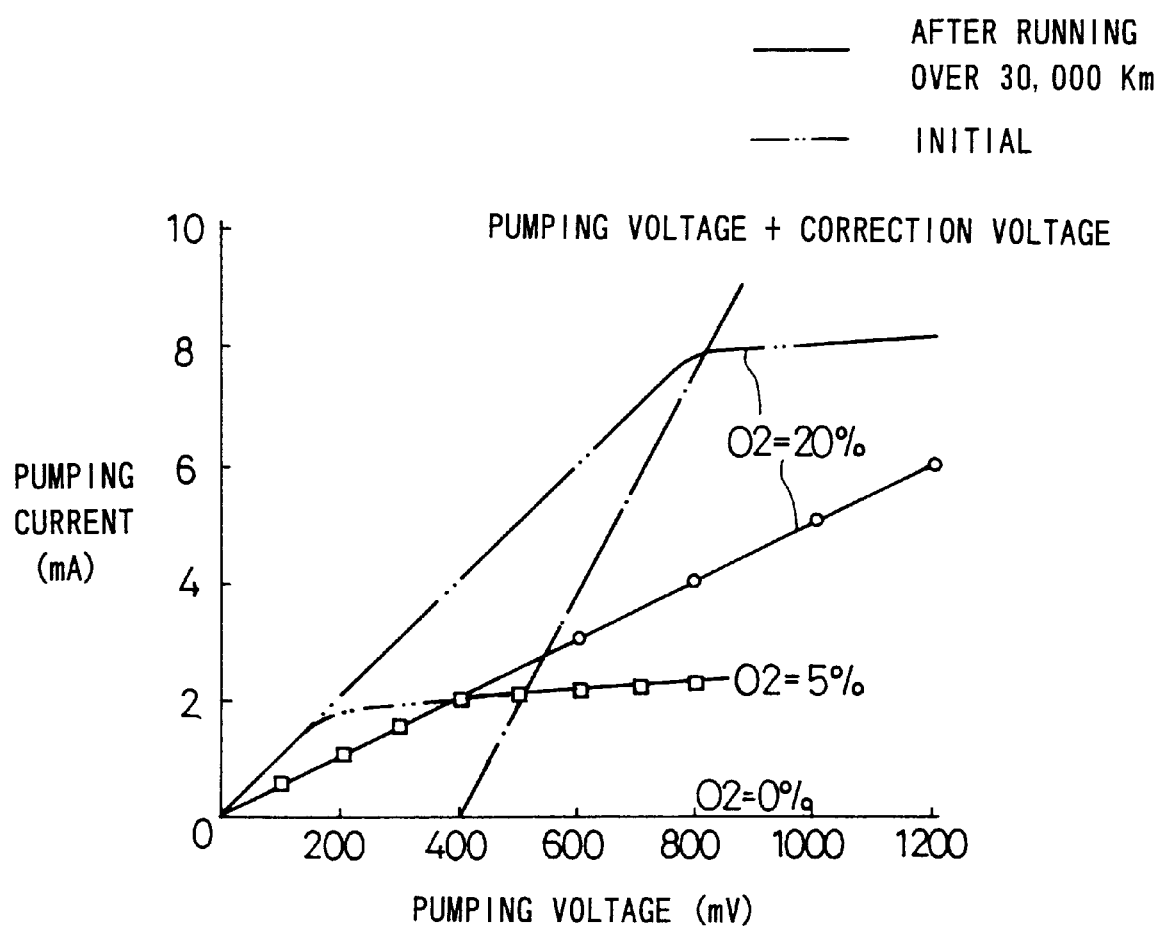
FIG. 9 shows a limiting current characteristic of the conventional gas sensor, illustrating a state of correction after test car running over 30,000 km by using a test car having a 2.0 L in-line 4-cylinder engine.
Figure 10:
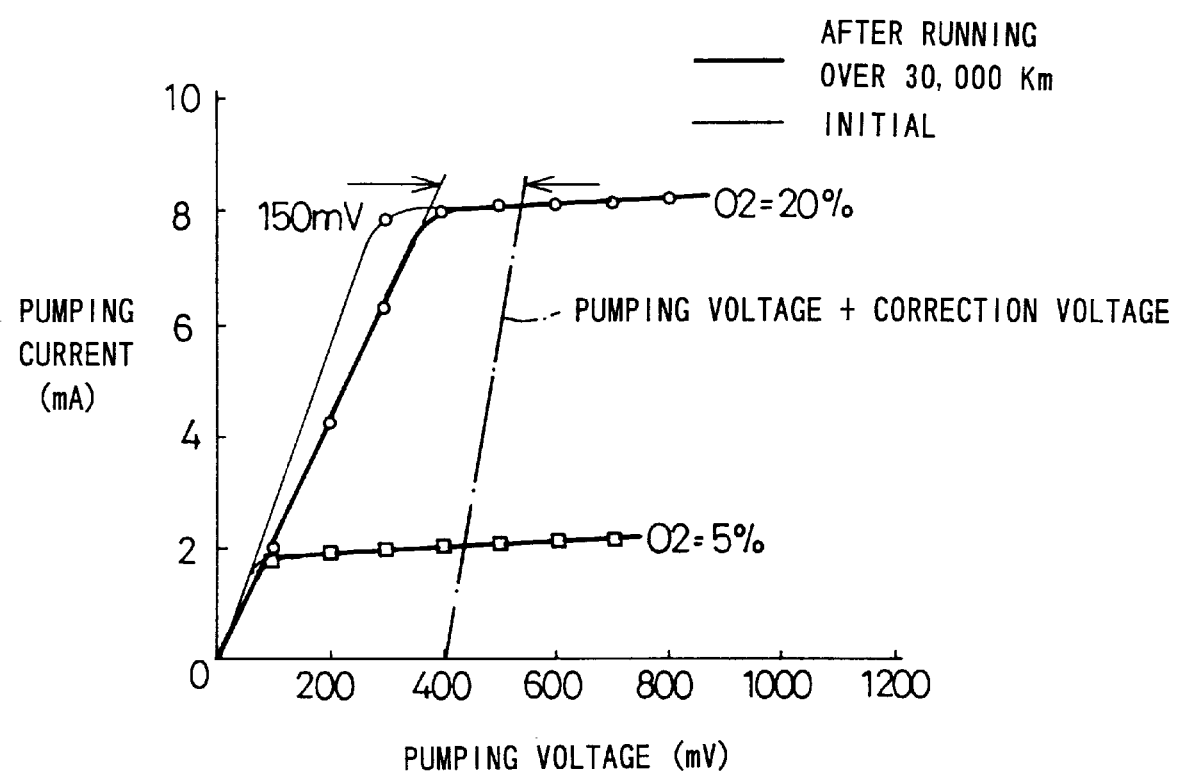
FIG. 10 shows a limiting current characteristic of the gas sensor constructed for the purpose of comparison, illustrating a state of correction after test car running over 30,000 km by using a test car having a 2.0 L in-line 4-cylinder engine.
Figure 11:
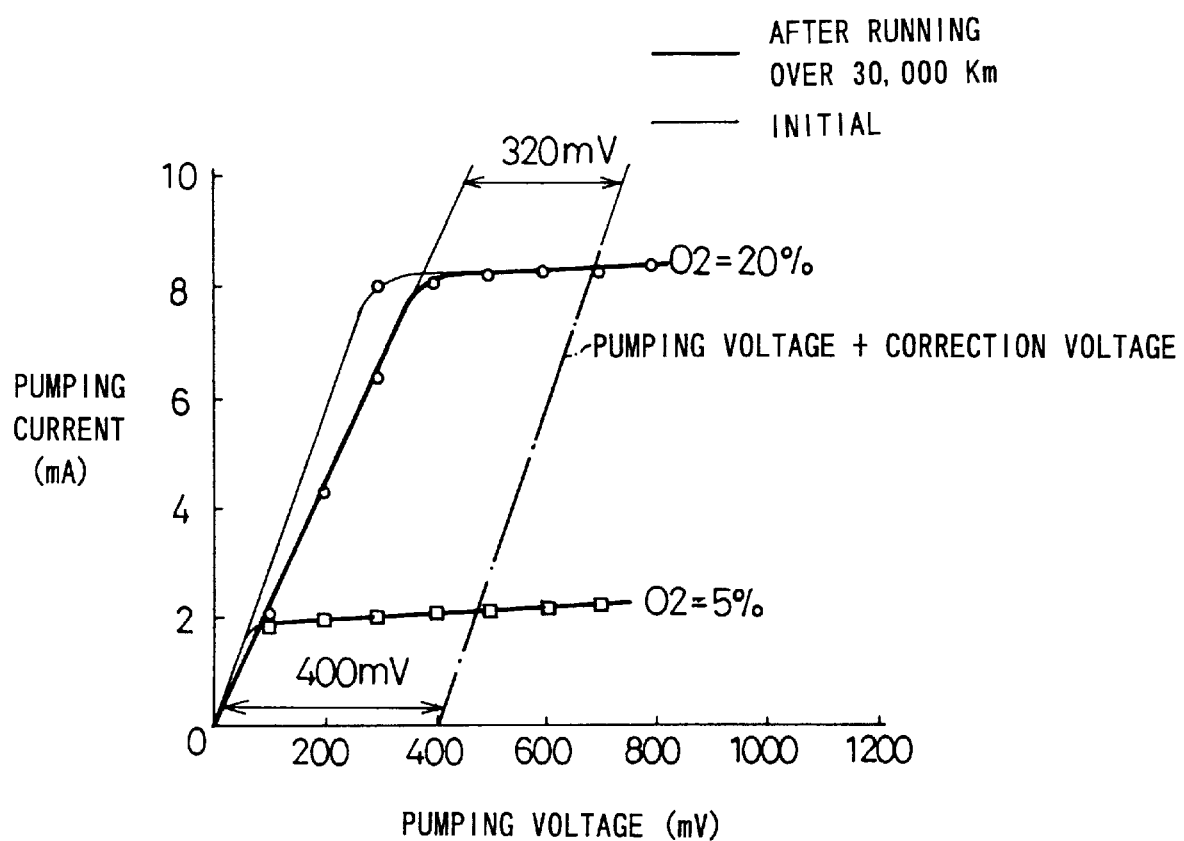
FIG. 11 shows a limiting current characteristic of the gas sensor according to the embodiment of the present invention, illustrating a state of correction after test car running over 30,000 km by using a test car having a 2.0 L in-line 4-cylinder engine.

FIGS. 9 to 11 illustrate states of correction after test car running over 30,000 km by using a test car having a 2.0 L in-line 4-cylinder engine respectively. FIG. 9 concerns the conventional gas sensor, FIG. 10 concerns the gas sensor constructed for the purpose of comparison (comparative example), and FIG. 11 concerns the gas sensor according to the embodiment of the present invention (working example). In FIG. 9, a two-dot chain line indicates a characteristic obtained at a stage of running start-up (initial stage), and a solid line indicates a characteristic obtained after running over 30,000 km. In FIGS. 10 and 11, thin solid lines indicate characteristics obtained at a stage of running start-up (initial stage), and thick solid lines indicate characteristics obtained after running over 30,000 km.

According to the characteristic curves shown in FIGS. 9 to 11, the following facts can be understood. Namely, in the case of the conventional gas sensor, no correction can be effected at all at a concentration of oxygen of 20%, and the operation point at the flat portion barely appears at a concentration of 5%. On the contrary, the working example undergoes the synergistic effect of the control for the pumping voltage Vp on the basis of the voltage between the inner pumping electrode 24a and the reference electrode 26, and the achievement of the ideal value of the correction voltage on the basis of the avoidance of oscillation owing to the capacitor C. Namely, in the case of the working example, the operation can be still performed in the vicinity of 320 mV of an amount corresponding to the electromotive force at the flat portion, even when the oxygen concentration in the measurement gas is 20% which is approximately the same as the oxygen concentration in the atmospheric air. Therefore, it is understood that the gas sensor according to the embodiment of the present invention is useful to perform the correction.

In general, the increase in impedance of the oxygen pump 22 during the course of use is principally caused by the increase in boundary resistance of the outer pumping electrode 24b. The gas sensor according to the embodiment of the present invention makes it possible to perform the correction with a value approximate to the ideal value, in addition to the fact that the correction is performed while neglecting the outer pumping electrode 24b. The synergistic effect of the foregoings makes it possible to maintain the high accuracy while using the simple arrangement even when the impedance of the oxygen pump 22 is increased during the course of use.

Next, several modified embodiments of the gas sensor according to the first embodiment will be explained with reference to FIGS. 12 to 14. Components or parts corresponding to those shown in FIG. 6 are designated by the same reference numerals, duplicate explanation of which will be omitted.

Figure 6:
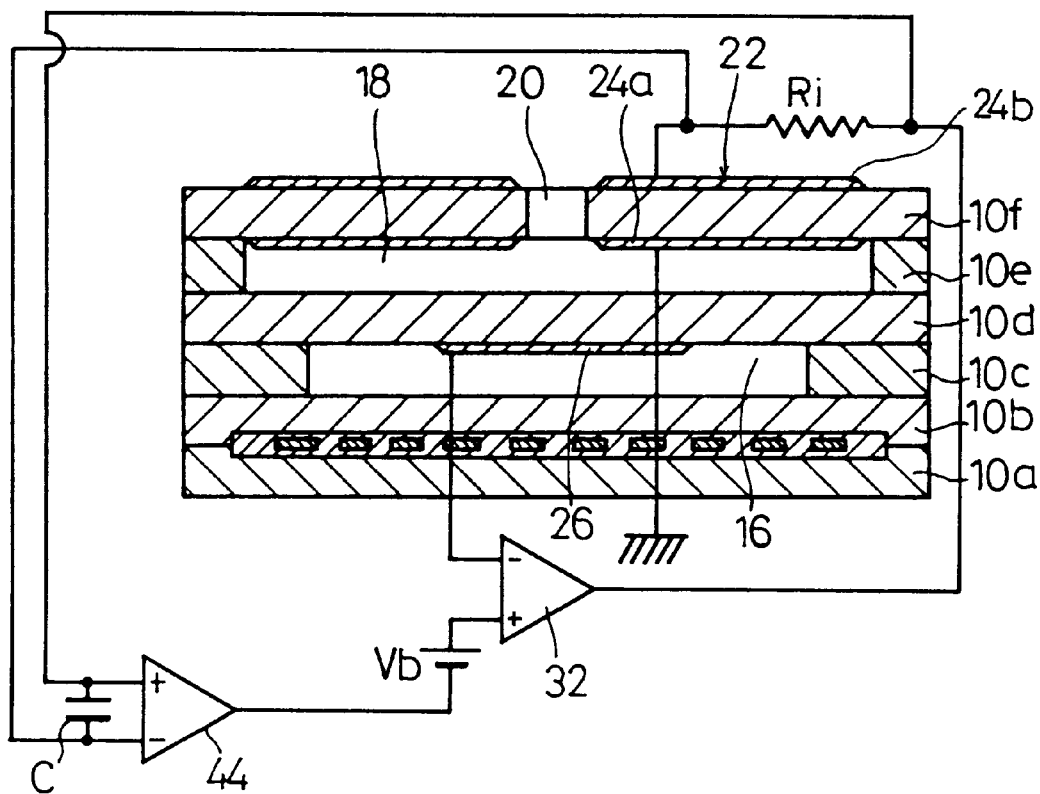
FIG. 6 shows a schematic arrangement of a first illustrative embodiment in which the gas sensor according to the present invention is applied to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm (hereinafter simply referred to as "gas sensor according to the first embodiment").
Figure 12:
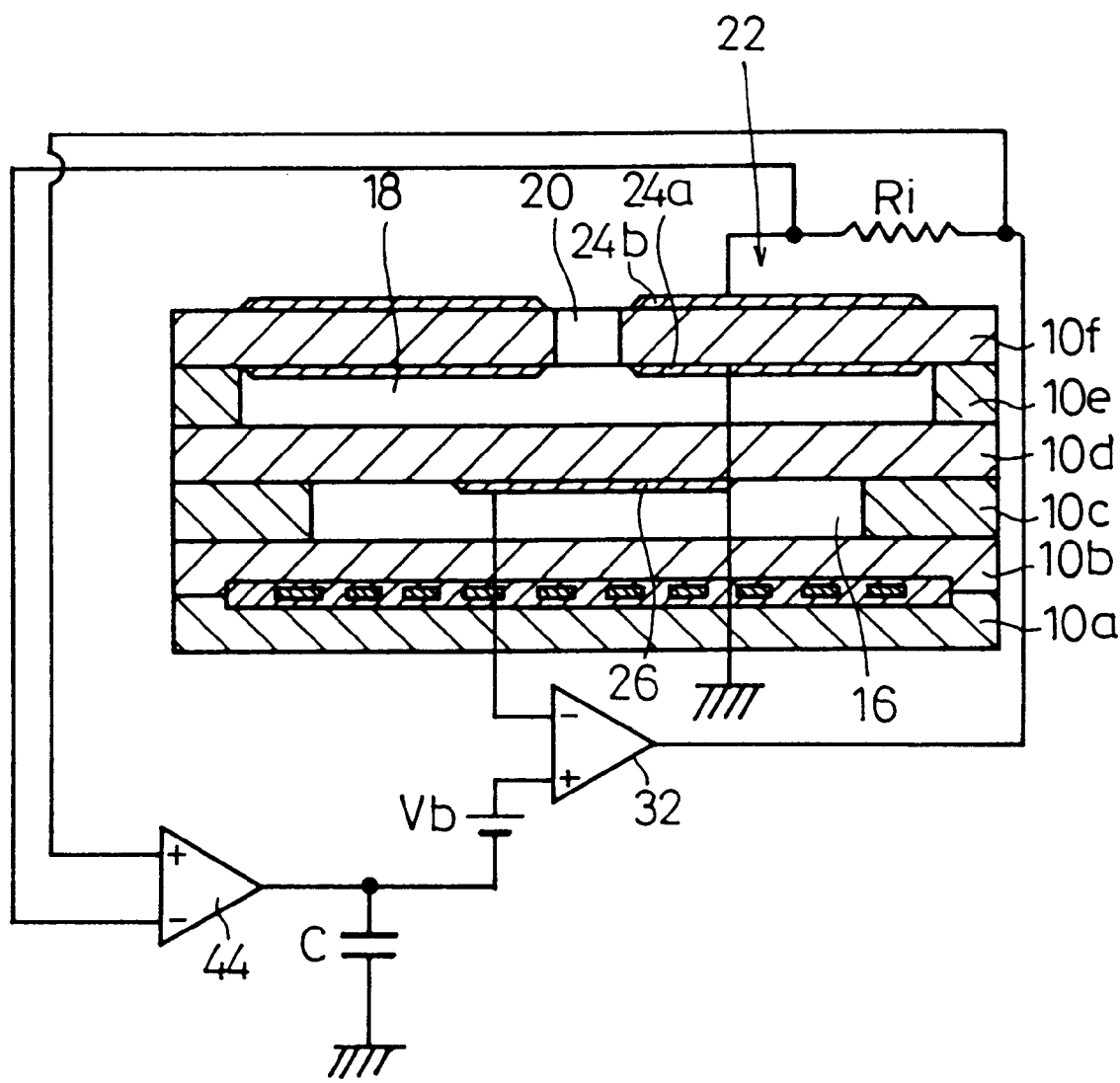
FIG. 12 shows an arrangement of a first modified embodiment concerning the gas sensor according to the first embodiment of the present invention.

At first, as shown in FIG. 12, a gas sensor according to a first modified embodiment is constructed substantially in the same manner as the gas sensor according to the embodiment of the present invention shown in FIG. 6. However, the former is different from the latter in that the capacitor C is connected between the output terminal of the differential amplifier 44 and the ground. The gas sensor according to the first modified embodiment also provides an effect equivalent to that obtained by the gas sensor according to the embodiment of the present invention. In this modified embodiment, in general, the output impedance of the differential amplifier 44 is extremely low. Therefore, it is necessary to set a large capacitance of the capacitor C in order to provide a sufficient spike-removing effect. It is desirable to adopt arrangements concerning second and third modified embodiments described below.

Figure 13:
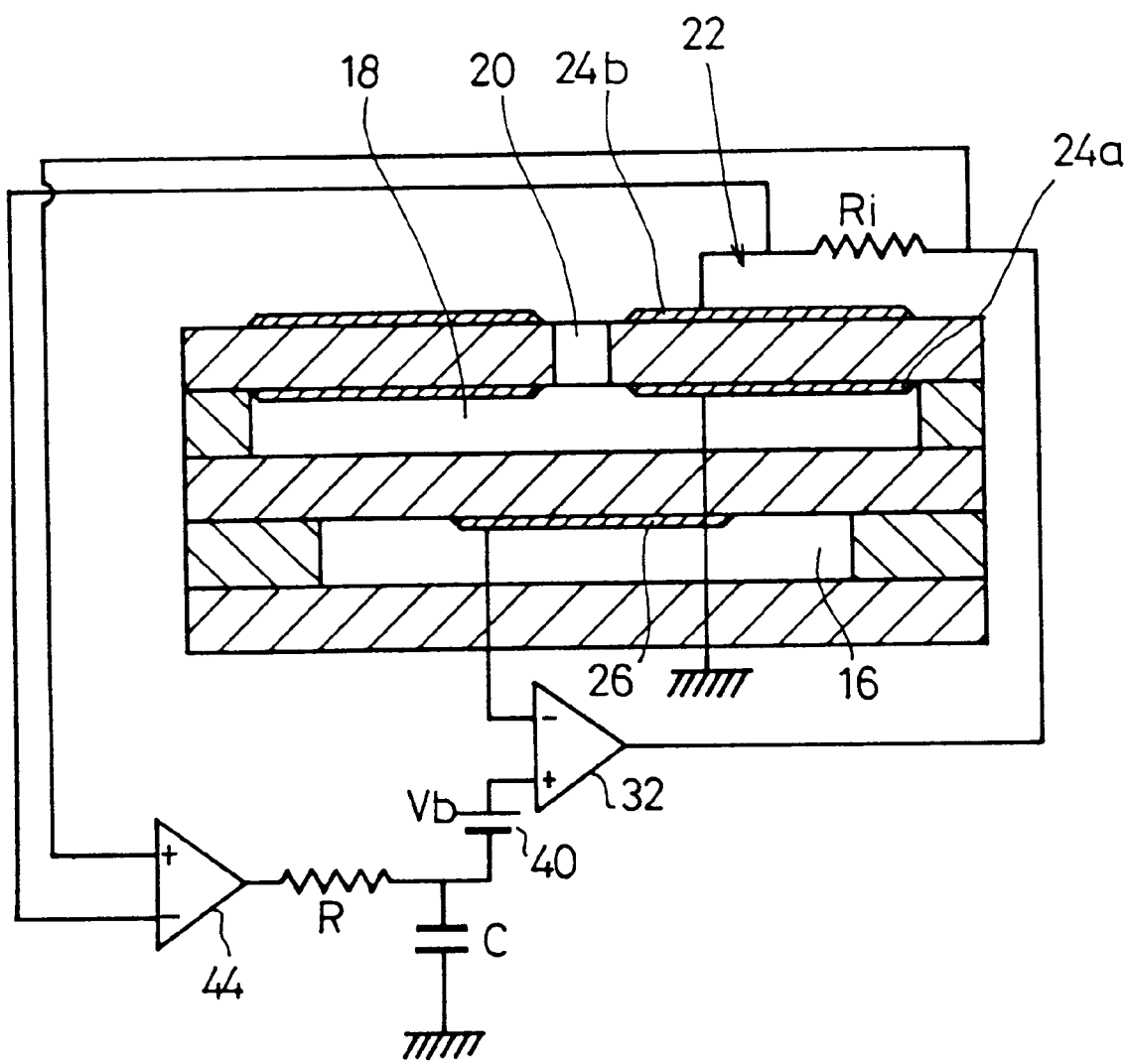
FIG. 13 shows an arrangement of a second modified embodiment concerning the gas sensor according to the first embodiment of the present invention.

Namely, as shown in FIG. 13, in a gas sensor according to the second modified embodiment, the resistor R is inserted and connected between the output terminal of the differential amplifier 44 and the generating source (power source 40) of the reference voltage Vb, and the capacitor C is connected between an end of the resistor R on the side of the power source 40 and the ground.

In this modified embodiment, it is effective that the time constant composed of CR is not less than ⅕ of an oscillation period obtained when oscillation occurs without using the capacitor C. As a result of confirmation by using the same sample as that used in the experiment described above, the oscillation is stopped when the resistor R is 10 kΩ, and the capacitor C is 1 μF, namely when the time constant is 10 msec, with respect to an oscillation period of 50 msec.

Figure 14:
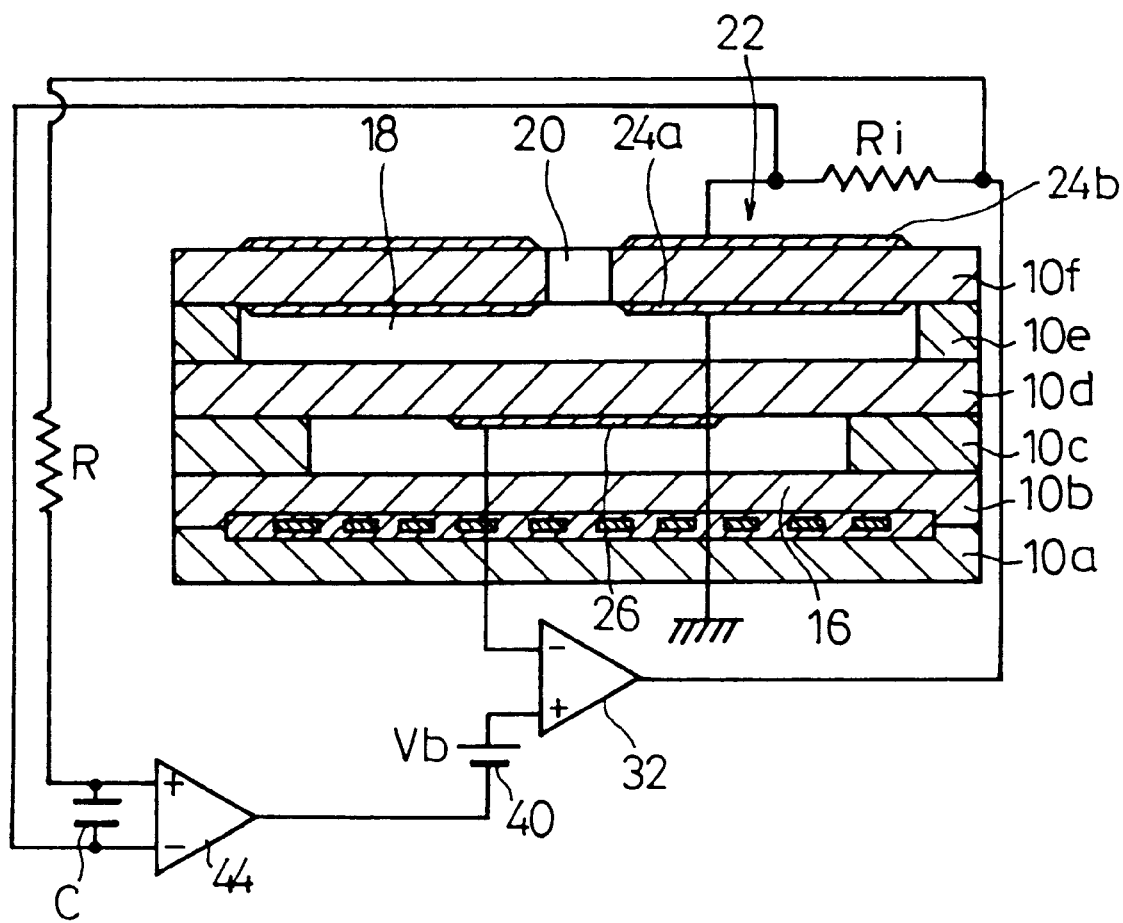
FIG. 14 shows an arrangement of a third modified embodiment concerning the gas sensor according to the first embodiment of the present invention.

In a gas sensor according to the third embodiment, as shown in FIG. 14, the resistor R is connected in series to the non-inverting input terminal of the differential amplifier 44, and the capacitor C is connected between the non-inverting input terminal and the inverting input terminal of the differential amplifier 44 located downstream therefrom. In this modified embodiment, the time constant composed of CR is approximately the same as that of the gas sensor according to the second modified embodiment.

Figure 15:
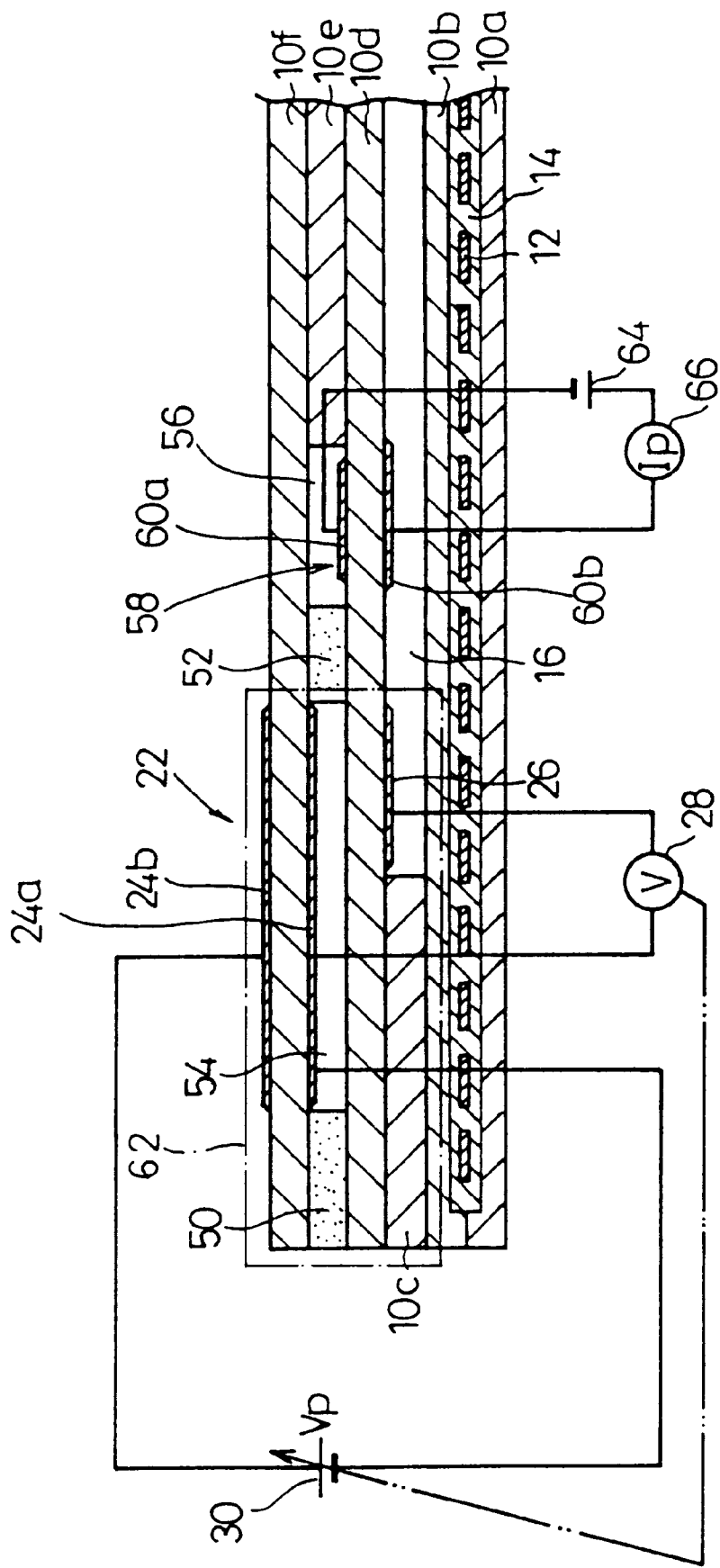
FIG. 15 shows a schematic arrangement of a second illustrative embodiment in which the gas sensor according to the present invention is applied to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm (hereinafter simply referred to as "gas sensor according to the second embodiment").

Next, a gas sensor according to the second embodiment of the present invention will be explained with reference to FIG. 15.

The gas sensor according to the second embodiment is substantially the same as the gas sensor according to the first embodiment in that the gas sensor comprises, for example, six stacked solid electrolyte layers 10a to 10f composed of ceramics based on the use of oxygen ion-conductive solid electrolytes such as $ZrO_2$, and the six solid electrolyte layers 10a to 10f are formed to have a lengthy plate-shaped configuration respectively. However, the former is different from the latter in that a second spacer layer 10e is interposed between the first and second solid electrolyte layers 10d, 10f, and first and second diffusion rate-determining sections 50, 52 are interposed between the first and second solid electrolyte layers 10d, 10f.

A first chamber 54 for adjusting the partial pressure of oxygen in a measurement gas is formed and comparted by a lower surface of the second solid electrolyte layer 10f, side surfaces of the first and second diffusion rate-determining sections 50, 52, and an upper surface of the first solid electrolyte layer 10d. A second chamber 56 for measuring oxides, for example, nitrogen oxides (NOx) in the measurement gas is formed and comparted by a lower surface of the second solid electrolyte layer 10f, a side surface of the second diffusion rate-determining section 52, side surfaces of the second spacer layer 10e, and an upper surface of the first solid electrolyte layer 10d. The first chamber 54 communicates with the second chamber 56 through the second diffusion rate-determining section 52.

A first electrode (upper pumping electrode 60a) for constructing a second oxygen pump 58 as described later on is formed on a portion of the upper surface of the first solid electrolyte layer 10d for forming the second chamber 56. A second electrode (lower pumping electrode 60b) for constructing the second oxygen pump 58 is formed on a portion of the first solid electrolyte layer 10d for forming the reference gas-introducing space 16, the portion being different from the portion for the reference electrode 26.

The first and second diffusion-rate determining sections 50, 52 give predetermined diffusion resistances to the measurement gas to be introduced into the first and second chambers 54, 56 respectively. Each of the first and second diffusion-rate determining sections 50, 52 can be formed as a passage composed of, for example, a porous material, or a small hole having a predetermined cross-sectional area so that the measurement gas may be introduced.

In the gas sensor according to this embodiment, the pumping voltage Vp, which is set on the basis of the electric potential difference V detected by the potentiometer 28, is applied between the inner pumping electrode 24a and the outer pumping electrode 24b provided for the first chamber 54, by the aid of the variable power source 30, in the same manner as described above. Oxygen is pumped out from or pumped in into the first chamber 54 by the oxygen pump 22 in accordance with application of the pumping voltage Vp. Accordingly, the partial pressure of oxygen in the first chamber 54 is set to have a predetermined value. Namely, the gas sensor includes an oxygen concentration controller 62 which is constructed by the first chamber 54, the oxygen pump 22, the reference electrode 26, and the reference gas-introducing space 16. Substantial operation for measuring nitrogen oxides is performed in the second chamber 56.

Brief explanation will be made below for the principle of measurement performed by the gas sensor according to the second embodiment. The pumping voltage Vp is applied by using the oxygen pump 22 of the oxygen concentration controller 62 so that the oxygen concentration in the first chamber 54 is in a degree to prevent NOx from decomposition, for example, at $10^{-7}$ atm. The purpose to prevent NOx from decomposition at $10^{-7}$ atm is achieved by using a material having low NOx reducibility, for example, an alloy of Au and Pt for the inner pumping electrode 24a.

The oxygen concentration in the first chamber 54 is detected on the basis of the terminal voltage between the inner pumping electrode 24a of the oxygen pump 22 and the reference electrode 26, in the same manner as performed in the gas sensor according to the first embodiment described above. The pumping voltage Vp is controlled and applied to the oxygen pump 22 so that the terminal voltage approaches the reference voltage Vb, namely, the oxygen concentration in the first chamber is approximately zero.

Accordingly, nitrogen monoxide (NO) remains in the first chamber 54. NO remained in the first chamber 54 passes through the second diffusion rate-determining section 52, and it flows into the next second chamber 56. In the second chamber 56, introduced NO is decomposed into N and 0, and the concentration of oxygen O is measured to indirectly determine the concentration of NO. The purpose to cause decomposition of NO is achieved by using a material having NOx reducibility, for example, Rh and Pt for the upper pumping electrode 60a.

The measurement of the oxygen O is performed by measuring the current flowing between the upper pumping electrode 60a and the lower pumping electrode 60b. Specifically, a pumping power source 64 is connected between the lower pumping electrode 60b and the upper pumping electrode 60a so that the current flows in a direction to pump out oxygen $O_2$ from the second chamber 56. During this process, when no oxygen exists in the second chamber 56, migration of oxygen (oxygen pumping out) is not performed between the both electrodes 60a, 60b. Therefore, no current flows between the both electrodes 60a, 60b. When oxygen exists in the second chamber 56, the current flows between the both electrodes 60a, 60b in accordance with the pumping out operation for oxygen. Therefore, the oxygen concentration in the second chamber 56 can be measured by inserting and connecting an ammeter 66 to the pumping power source 64 in series to measure a current value thereof. The current value is proportional to the amount of pumped out oxygen. Accordingly, the amount of NO can be determined from the current value. Accordingly, $NO_2$ can be simultaneously measured equivalently.

Namely, the gas sensor according to the second embodiment is operated as follows. The oxygen concentration in the measurement gas is made to have a low constant value in the first chamber 54. Bound oxygen is decomposed by the aid of the catalyst or electrolysis in the second chamber 56. Oxygen produced during the decomposition is pumped out by using the second oxygen pump 58. The current, which flows during the pumping out operation, is measured. Thus the concentration of the gas component containing bound oxygen is measured.

When NOx is measured as the gas component containing bound oxygen, it is preferable to decompose NOx by the aid of the catalyst in the second chamber 56. When $H_2O$ and $CO_2$ are measured, it is preferable to perform the operation by the aid of the electrolysis.

When an inflammable gas component such as HC is measured, the operation is performed as follows. At first, the pumping voltage is applied so that the oxygen concentration in the first chamber 54 is at a level, for example, $10^{-15}$ atm at which the inflammable gas component does not burn. The pumping power source is connected in a direction to pump in oxygen into the second chamber 56 so that the inflammable gas component is allowed to burn. During this process, the amount of the inflammable gas can be determined by measuring the amount of oxygen required for the inflammable gas component to burn, i.e., the pumping current.

The gas sensor according to the second embodiment is constructed in the same manner as the gas sensor according to the first embodiment as follows. Namely, the voltage between the inner pumping electrode 24a and the reference electrode 26 of the oxygen concentration controller 62 is measured to determine a difference between the measured voltage and the reference voltage. The pumping voltage Vp is controlled by using the differential voltage.

Figure 16:
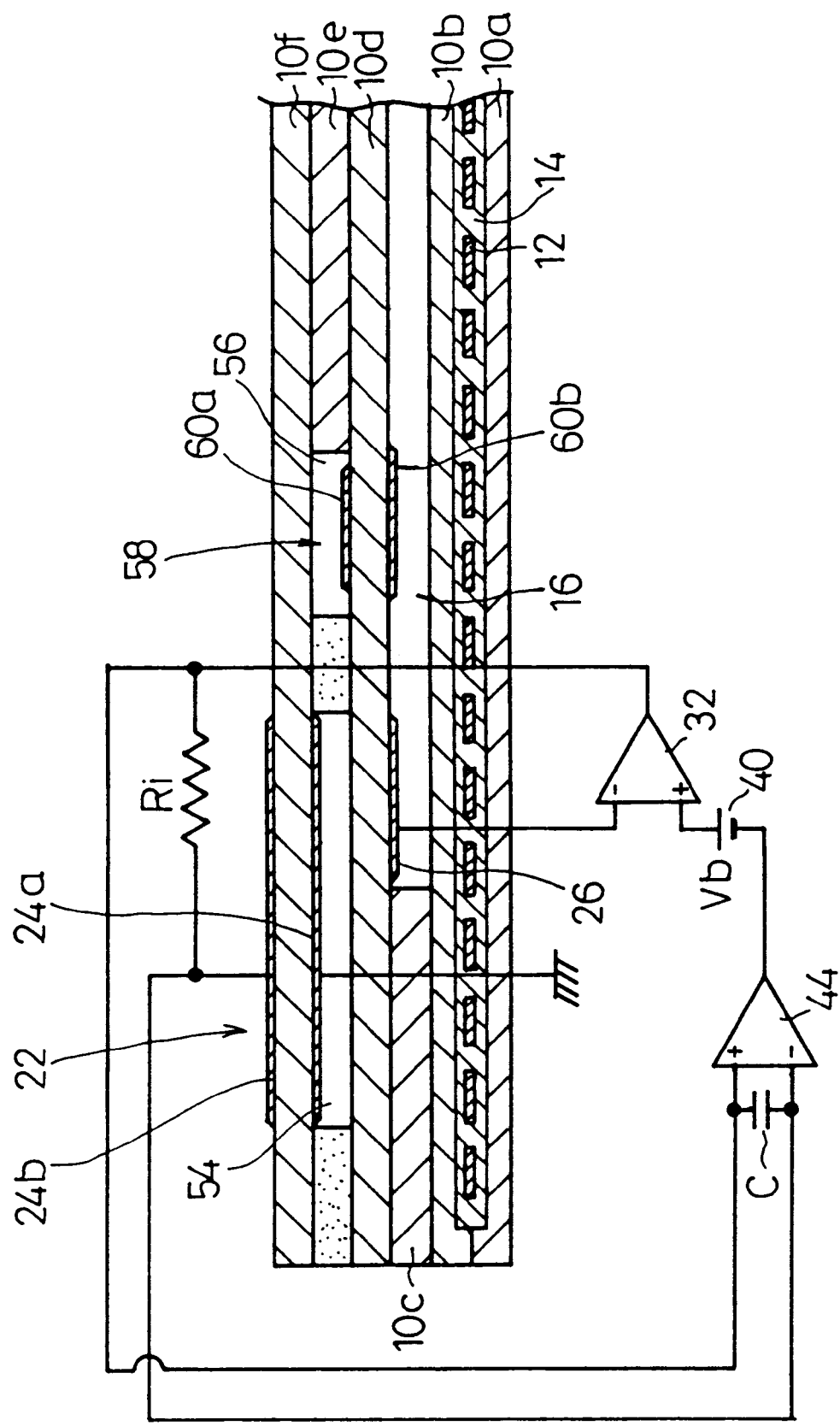
FIG. 16 shows a specified arrangement of the gas sensor according to the second embodiment.
Figure 17:
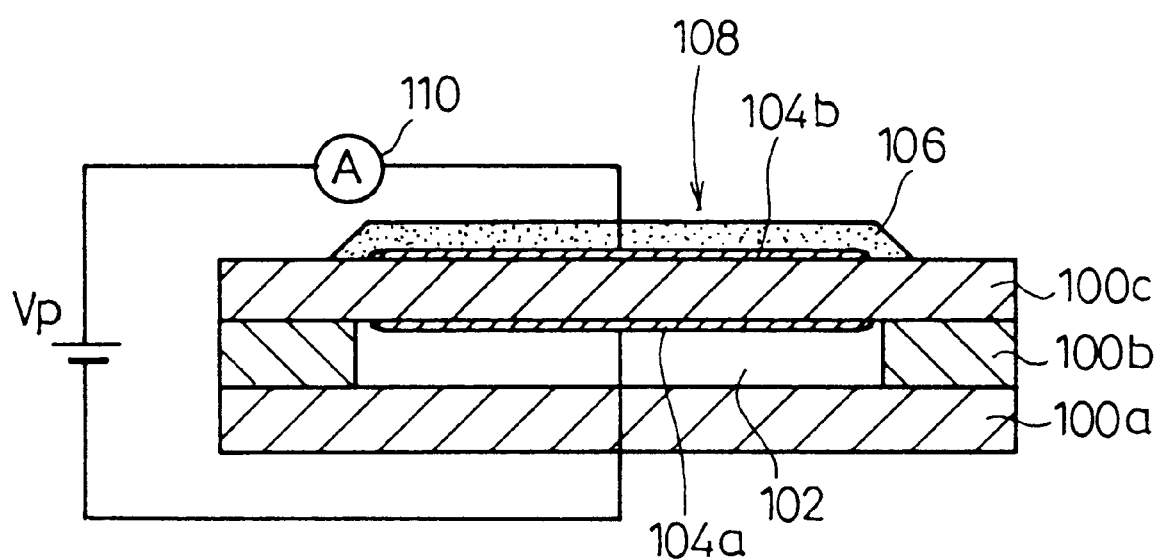
FIG. 17 shows an arrangement illustrating a limiting current type oxygen sensor based on the use of the conventional oxygen pump.
Figure 18:
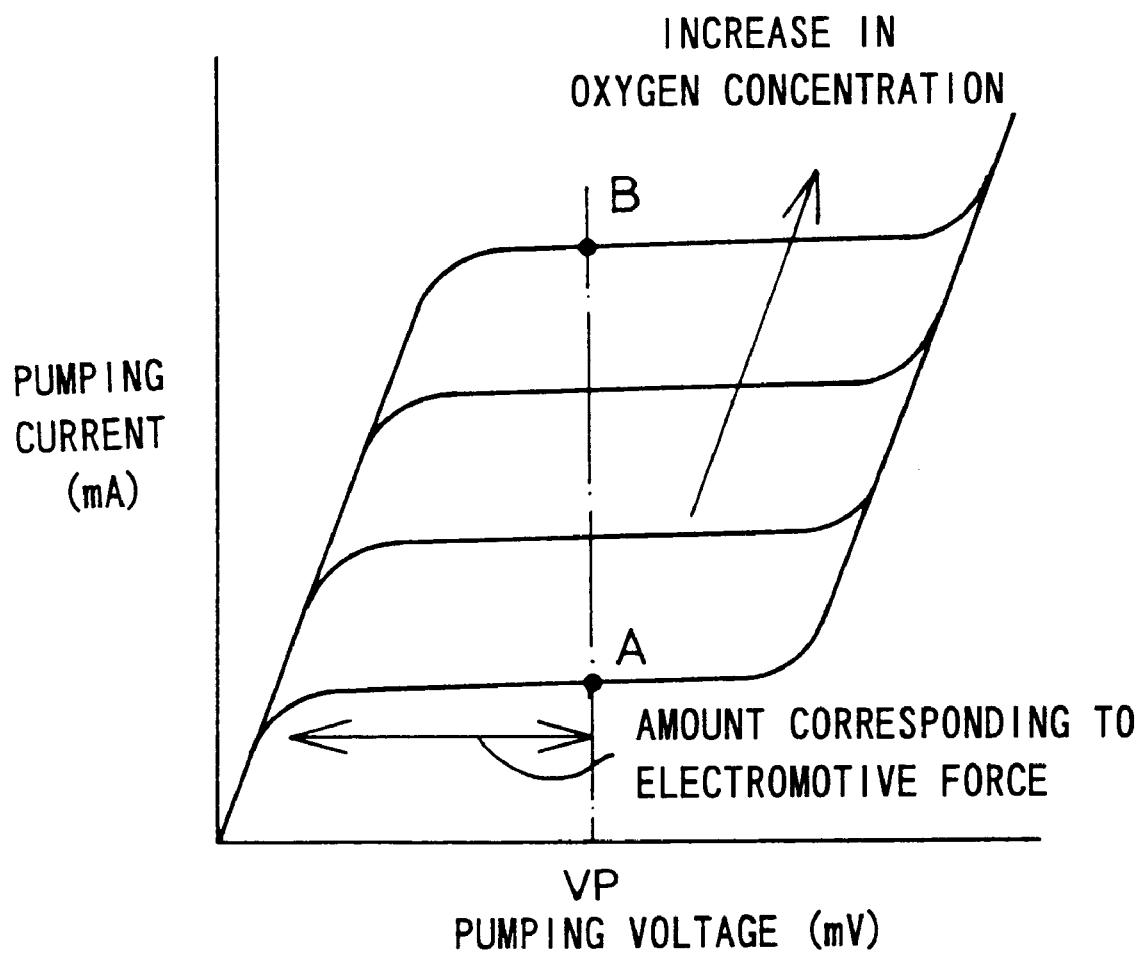
FIG. 18 shows a limiting current characteristic of the limiting current type oxygen sensor based on the use of the conventional oxygen pump.
Figure 19:
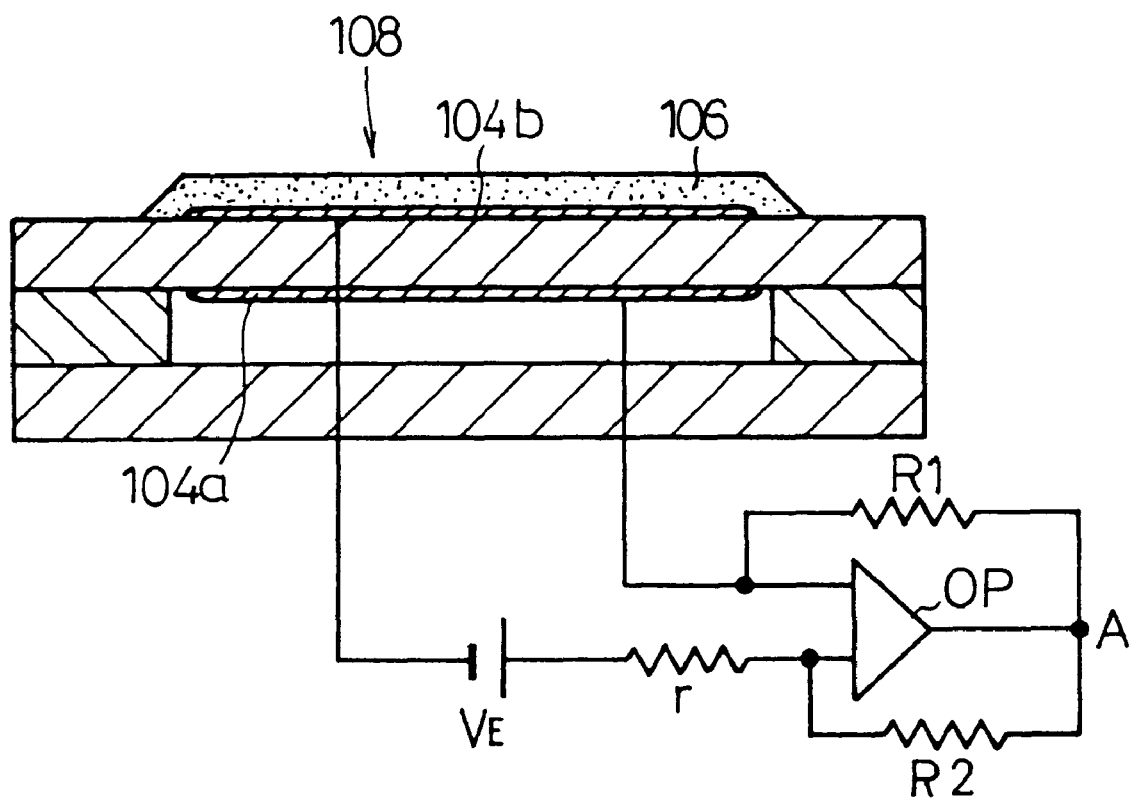
FIG. 19 shows an arrangement of another conventional gas sensor.
Figure 20:
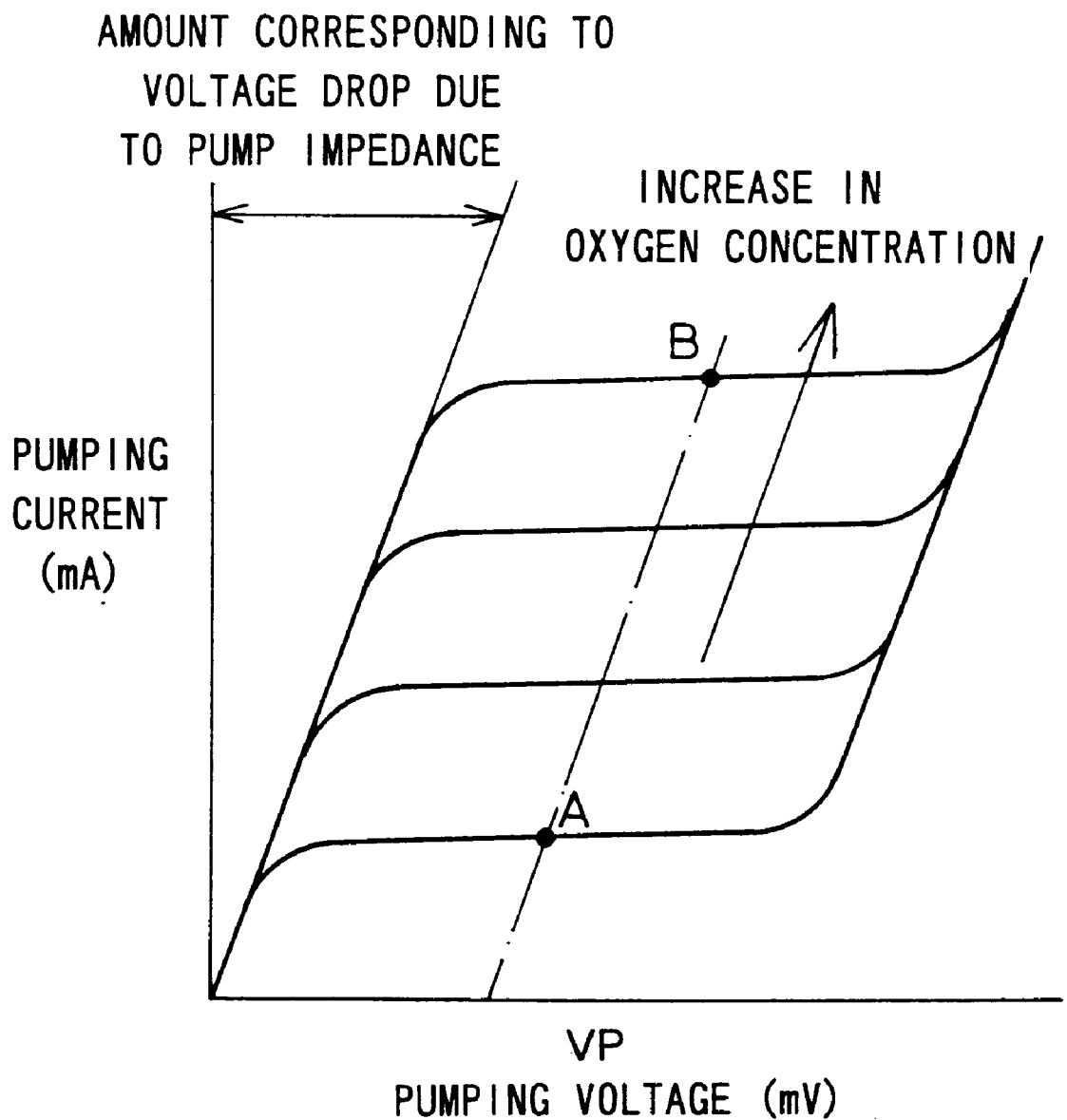
FIG. 20 shows a limiting current characteristic of the another conventional gas sensor.

Specifically, the gas sensor according to the second embodiment is wired and connected as shown in FIG. 16, comprising a comparative amplifier 32 for comparing the reference voltage Vb with the terminal voltage between the reference electrode 26 and the inner pumping electrode 24a, and amplifying a different therebetween with a predetermined gain to make an output. The output voltage (differential voltage) from the comparative amplifier 32 is applied, as the pumping voltage Vp supplied to the oxygen pump 22, between the inner pumping electrode 24a and the outer pumping electrode 24b. A resistor Ri for detecting the pumping current is inserted and connected between the output terminal of the comparative amplifier 32 and the outer pumping electrode 24b of the oxygen pump 22. Both ends of the resistor Ri for detecting the pumping current form a short circuit with a capacitor C inserted therebetween. Further, one electrode of the capacitor C is connected to a non-inverting terminal of a differential amplifier 44, and the other electrode of the capacitor C is connected to an inverting terminal of the differential amplifier 44.

In the gas sensor according to the second embodiment, the terminal voltage (measured voltage), which is applied to the inverting terminal of the comparative amplifier 32, is the terminal voltage between the inner pumping electrode 24a of the oxygen pump 22 and the reference electrode 26 in the reference gas-introducing space 16. Therefore, the change in oxygen concentration in the first chamber 54 appears without any time delay as the change in terminal voltage between the inner pumping electrode 24a of the oxygen pump 22 and the reference electrode 26. Accordingly, it is possible to effectively suppress the oscillation phenomenon in the feedback control.

Further, the resistor Ri for detecting the pumping current and the capacitor C provide a time constant which realizes an arrangement in which a phase-compensating circuit for proportional integral operation is inserted and connected to the feedback control system for the pumping voltage Vp. Thus it is possible to effectively suppress the spike-shaped noise generated in the output voltage of the differential amplifier 44, i.e., in the correction voltage. This results in high accuracy of the adjustment for the pumping voltage Vp, performed by the comparative amplifier 32. Accordingly, it is possible to accurately measure the oxygen concentration in the measurement gas introduced into the first chamber 54.

It is possible for the gas sensor according to the second embodiment to adopt the arrangement of the first, second, or third modified embodiment of the gas sensor according to the first embodiment of the present invention.

It is a matter of course that this invention is not limited to the embodiments described above, which can be constructed in other various forms without deviating from the gist or essential characteristics of this invention.

What is claimed is:

1. A gas sensor comprising:
    a first space surrounded by first, second and third substrates composed of solid electrolytes, for introducing a measurement gas thereinto;
    a gas-pumping means including inner and outer electrodes formed inside and outside said first space surrounded by said substrates respectively, said third substrate interposed by said both electrodes, and a pumping power source for applying, between said both electrodes, a control voltage for pumping out a predetermined gas component;
    a second space surrounded by substrates composed of solid electrolytes, for introducing a reference gas thereinto;
    a measuring means for measuring a terminal voltage between a reference electrode formed on said first substrate and disposed on a side of said second space and said inner electrode of said gas-pumping means;
    a first control voltage-adjusting means for adjusting a level of said control voltage on the basis of said terminal voltage;
    a second control voltage-adjusting means for detecting a current flowing through said gas-pumping means when said gas component is pumped out by said gas-pumping means, and reflecting an obtained value of said current in said adjustment for said level of said control voltage performed by said first control voltage-adjusting means; and
    a spike-suppressing means for suppressing a spike signal generated in said second control voltage-adjusting means.

2. The gas sensor according to claim 1, wherein said first control voltage-adjusting means is provided with a comparing means for determining a deviation between said terminal voltage and a comparative voltage, and said level of said control voltage is adjusted on the basis of said deviation obtained by said comparing means.

3. The gas sensor according to claim 2, wherein said second control voltage-adjusting means is provided with a resistor for detecting said current flowing through said gas-pumping means and converting said current into a voltage when said gas component is pumped out by said gas-pumping means, and an amplifier for amplifying said voltage resulting when the resistor converts said current into a voltage with a predetermined gain and superimposing an obtained voltage on said comparative voltage.

4. The gas sensor according to claim 3, wherein said spike-suppressing means is provided with a capacitor connected between
    (a) a resistor for detecting said current flowing through said gas-pumping means and converting said current into a voltage when said gas component is pumped out by said gas-pumping means, and
    (b) said amplifier for amplifying said voltage resulting when the resistor converts said current into a voltage for detecting said current flowing through said gas-pumping means and converting said current into said voltage when said gas component is pumped out by said gas-pumping means, with said predetermined gain and superimposing said obtained voltage on said comparative voltage, and said sensor having a generating source of said comparative voltage.

5. The gas sensor according to claim 2, wherein said spike-suppressing means is provided with a capacitor connected between
    (a) a resistor serially connected to a resistor for detecting said current flowing through said gas-pumping means and converting said current into a voltage when said gas component is pumped out by said gas-pumping means, and
    (b) an amplifier for amplifying said voltage resulting when the resistor for detecting the current flowing through said gas-pumping means converts said current into a voltage with a predetermined gain and superimposing an obtained voltage on said comparative voltage.

6. The gas sensor according to claim 1, wherein said spike-suppressing means is provided with a capacitor connected to both ends of a resistor for detecting said current flowing through said gas-pumping means and converting said current into a voltage when said gas component is pumped out by said gas-pumping means.

7. The gas sensor according to claim 1, wherein a gas diffusion rate-determining section for giving a predetermined diffusion resistance to said measurement gas is provided at a passage for introducing said measurement gas into said first space.

8. The gas sensor according to claim 1, further comprising:
    a third space for introducing said measurement gas in said first space thereinto;
    a second gas diffusion-rate determining section provided at a passage for introducing said measurement gas into said third space, for giving a predetermined diffusion resistance to said measurement gas;
    a measurement gas-decomposing means disposed in said third space, for decomposing and degrading said predetermined gas component in said measurement gas; and a gas component-detecting means for detecting said predetermined gas component decomposed and degraded by said measurement gas-decomposing means.

9. The gas sensor according to claim 1, further comprising:
   a third space for introducing said measurement gas in said first space thereinto;
   a second gas diffusion-rate determining section provided at a passage for introducing said measurement gas into said third space, for giving a predetermined diffusion resistance to said measurement gas;
   a gas component supply means for feeding said predetermined gas component to said third space; and
   a gas component-detecting means for detecting said gas component fed by said gas component supply means.

10. A gas concentration controller comprising: a first space surrounded by first, second and third substrates composed of solid electrolytes, for introducing a measurement gas thereinto;
   a gas diffusion rate-determining section provided at a passage for introducing said measurement gas into said first space, for giving a predetermined diffusion resistance to said measurement gas;
   a gas-pumping means including inner and outer electrodes formed inside and outside said first space surrounded by said substrates respectively, said third substrate interposed by said both electrodes, and a pumping power source for applying, between said both electrodes, a control voltage for pumping out a predetermined gas component;
   a second space surrounded by substrates composed of solid electrolytes, for introducing a reference gas thereinto;
   a measuring means for measuring a terminal voltage between a reference electrode formed on said first substrate and disposed on a side of said second space and said inner electrode of said gas-pumping means;
   a first control voltage-adjusting means for adjusting a level of said control voltage on the basis of said terminal voltage;
   a second control voltage-adjusting means for detecting a current flowing through said gas-pumping means when said gas component is pumped out by said gas-pumping means, and reflecting an obtained value of said current in said adjustment for said level of said control voltage performed by said first control voltage-adjusting means; and
   a spike-suppressing means for suppressing a spike signal generated in said second control voltage-adjusting means.

11. The gas concentration controller according to claim 10, wherein said first control voltage-adjusting means is provided with a comparing means for determining a deviation between said terminal voltage and a comparative voltage, and said level of said control voltage is adjusted on the basis of said deviation obtained by said comparing means.

12. The gas concentration controller according to claim 11, wherein said second control voltage-adjusting means is provided with a resistor for detecting said current flowing through said gas-pumping means and converting said current into a voltage when said gas component is pumped out by said gas-pumping means, and an amplifier for amplifying said voltage resulting when the resistor converts said current into a voltage with a predetermined gain and superimposing an obtained voltage on said comparative voltage.

13. The gas concentration controller according to claim 12, wherein said spike-suppressing means is provided with a capacitor connected between
   (a) a resistor for detecting said current flowing through said gas-pumping means and converting said current into a voltage when said gas component is pumped out by said gas-pumping means, and
   (b) an amplifier for amplifying said voltage resulting when the resistor converts said current into a voltage for detecting said current flowing through said gas-pumping means and converting said current into said voltage when said gas component is pumped out by said gas-pumping means, with a predetermined gain and superimposing an obtained voltage on said comparative voltage, and said gas concentration controller having a generating source of said comparative voltage.

14. The gas concentration controller according to claim 11, wherein said spike-suppressing means is provided with a capacitor connected between
   (a) a resistor for detecting said current flowing through said gas-pumping means and converting said current into a voltage when said gas component is pumped out by said gas-pumping means, and
   (b) an amplifier for amplifying said voltage resulting when the resistor converts said current into a voltage with a predetermined gain and superimposing an obtained voltage on said comparative voltage.

15. The gas concentration controller according to claim 10, wherein said spike-suppressing means is provided with a capacitor connected to both ends of a resistor for detecting said current flowing through said gas-pumping means and converting said current into a voltage when said gas component is pumped out by said gas-pumping means.

* * * * *